(12) United States Patent
Belacazar et al.

(10) Patent No.: US 8,005,551 B2
(45) Date of Patent: Aug. 23, 2011

(54) IMPLANTABLE MEDICAL LEAD

(75) Inventors: Hugo A. Belacazar, St. Paul, MN (US); James D. Reinke, Maple Grove, MN (US); Robert M. Ecker, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 297 days.

(21) Appl. No.: 12/350,382

(22) Filed: Jan. 8, 2009

(65) Prior Publication Data

US 2009/0118808 A1   May 7, 2009

Related U.S. Application Data

(62) Division of application No. 10/947,813, filed on Sep. 23, 2004, now Pat. No. 7,493,174.

(51) Int. Cl.
*A61N 1/00* (2006.01)
(52) U.S. Cl. ............................................. 607/122
(58) Field of Classification Search .................. 607/122
See application file for complete search history.

(56) References Cited

U.S. PATENT DOCUMENTS

| 4,432,372 A | 2/1984 | Monroe |
| 4,467,807 A | 8/1984 | Bornzin |
| 4,750,495 A | 6/1988 | Moore et al. |
| 4,779,618 A * | 10/1988 | Mund et al. ..................... 607/22 |
| 4,813,421 A | 3/1989 | Baudino et al. |
| 4,903,701 A | 2/1990 | Moore et al. |
| 4,967,755 A | 11/1990 | Pohndorf |
| 5,040,538 A | 8/1991 | Mortazavi |
| 5,074,304 A | 12/1991 | Hedin |
| 5,309,918 A | 5/1994 | Schraag |
| 5,411,532 A | 5/1995 | Mortazavi |
| 5,514,171 A | 5/1996 | Hoegnelid |
| 5,535,752 A | 7/1996 | Halperin et al. |
| 5,843,135 A | 12/1998 | Weijand |
| 5,999,848 A | 12/1999 | Gord |
| 6,038,480 A * | 3/2000 | Hrdlicka et al. ............. 607/116 |
| 6,144,866 A | 11/2000 | Miesel et al. |
| 6,163,723 A | 12/2000 | Roberts et al. |
| 2002/0099423 A1 | 7/2002 | Berg |
| 2003/0088303 A1 | 5/2003 | Goode |
| 2005/0075674 A1* | 4/2005 | Zillmer et al. ..................... 607/9 |
| 2009/0192572 A1 | 7/2009 | Dal Molin et al. |

FOREIGN PATENT DOCUMENTS

WO   W09943381   9/1999

* cited by examiner

*Primary Examiner* — George Manuel
(74) *Attorney, Agent, or Firm* — Scott A. Bardell; Reed A. Duthler

(57) ABSTRACT

An implantable medical lead includes a device, such as a physiological sensor, that is coupled to one or more stimulation/sensing sensing conductors within the lead. When the implantable medical lead is coupled to an implantable medical device, the device carried by the lead both receives power from, and communicates with the implantable medical device via the one or more stimulation/sensing sensing conductors. Each of the one or more stimulation/sensing sensing conductors is also coupled to an electrode that is exposed to body tissue.

8 Claims, 13 Drawing Sheets

IMPLANTABLE MEDICAL LEAD

CROSS REFERENCE TO RELATED APPLICATIONS

This application is a divisional application of U.S. application Ser. No. 10/947,813 filed on Sep. 23, 2004, now U.S. Pat. No. 7,493,174, the disclosure of which is incorporated by reference in its entirety herein.

TECHNICAL FIELD

The invention relates to implantable medical leads and, more particularly, to implantable medical leads that include sensors.

BACKGROUND

A variety of implantable medical devices (IMDs) are available to monitor physiological conditions of a patient, deliver therapy to a patient, or both. Typically, an IMD is coupled to one or more implantable leads that include electrodes. An IMD senses and monitors physiological signals or delivers electrical stimulation through the electrodes. For example, cardiac pacemakers are coupled to one or more implantable leads that include sensing and stimulation electrodes to sense cardiac electrical activity and deliver cardiac pacing pulses.

In some cases, an IMD is additionally coupled to and communicates with one or more physiological sensors. For example, some cardiac pacemakers receive signals output by oxygen saturation sensors, oxygen or carbon dioxide partial pressure sensors, intracardiac or intravascular fluid pressure sensors, temperature sensors, or accelerometers. Cardiac pacemakers typically use the signals output by physiological sensors to control or adjust the pacing therapy delivered to a patient.

Typically, sensors are located some distance away from the IMD, such as within the heart or vascular system of a patient, and communicate with the IMD over a two-conductor bus. The use of separate physiological sensing leads, i.e., implantable leads in addition to the one or more implantable leads that carry sensing or stimulating electrodes, increases the volume of lead material implanted within a patient. Increased volume of lead material adds to the complexity of the implant procedure.

In order to avoid the use of separate physiological sensing leads, some implantable leads incorporate sensing or stimulating electrodes, as well as physiological sensors. Such leads typically include additional conductors, i.e., separate from the conductors that are coupled to the electrodes, to couple the physiological sensor to an IMD. The additional conductors are used to isolate the physiological sensor from the electrodes and the stimulation and sensing circuitry of the IMD. Isolation serves to avoid unintended stimulation of body tissue via the physiological sensor, and reduces interference with the electrical sensing functions of the IMD. However, the presence of additional conductors increases lead diameter and stiffness, which can in turn increase the difficulty of the implantation procedure.

SUMMARY

In general, the invention is directed to an implantable medical lead that includes a physiological sensor coupled to one or more stimulation/sensing sensing conductors within the lead, systems including such a lead, and related methods. When the lead is connected to an IMD, the sensor on the lead both receives power from, and communicates with the IMD via the one or more stimulation/sensing conductors. Each of the stimulation/sensing conductors is also coupled to an electrical stimulation or sensing electrode that is exposed to body tissue. However, in the present invention, the need for additional conductors is rendered unnecessary. Due to the absence of additional conductors, a lead according to the invention facilitates smaller diameter, greater flexibility and enhanced reliability relative to leads that include separate sets of conductors.

In some embodiments, the implantable medical lead includes at least two stimulation/sensing sensing conductors, each of which is coupled to a respective electrode. In such embodiments, the physiological sensor is coupled to the conductors in parallel with a current path between the electrodes. In other embodiments, the sensor is coupled to a single stimulation/sensing sensing conductor in series with a current path between an electrode coupled to the stimulation/sensing sensing conductor and another electrode not carried by the lead, such as an electrode integrated with a housing of the IMD that is connected to the lead. In exemplary embodiments, the IMD that is connected to the lead is a cardiac pacemaker that provides bipolar pacing and sensing via two stimulation/sensing sensing conductors and tip and ring electrodes, or unipolar pacing and sensing via a single stimulation/sensing sensing conductor, a tip electrode, and an electrode integrated with a housing of the pacemaker.

In some embodiments, a physiological sensor is powered or charged by a stimulation signal, e.g., cardiac pacing pulses, delivered by the IMD to the patient via the conductors and electrodes of the lead. In such embodiments, the IMD can increase the amplitude of the stimulation signal during periods in which the sensor is charged so that an adequate level of stimulation continues to be delivered to the patient. The IMD may also suspend autocapture functions during periods in which the sensor is charged to avoid difficulty in identifying a steady-state stimulation amplitude that may be caused by the varying load presented by the sensor when active.

In other embodiments, the IMD additionally or alternatively delivers power pulses on one or more conductors to power or charge the physiological sensor carried by the lead. In certain embodiments, the power pulses are sub-threshold pulses. In other words, the power pulses have an amplitude and/or width inadequate to cause undesired stimulation of the patient, such as undesired capture of cardiac tissue. In exemplary embodiments, the power pulses are also biphasic to avoid charge build up at the one or more electrodes.

In some embodiments in which the IMD comprises a cardiac pacemaker, the IMD delivers power pulses during a refractory period of the patient to avoid unintentional capture of cardiac tissue by the power pulses. Further, in embodiments in which the IMD delivers stimulation and power pulses on the one or more conductors, the sensor may selectively uncouple its energy storage element from the conductors to avoid presenting a load during delivery of stimulation. The IMD can provide a signal to the sensor indicating an upcoming delivery of stimulation that causes the sensor to uncouple the energy storage element in response to the signal.

The IMD and the physiological sensor carried by the lead communicate via the conductors. For example, the IMD communicates with the sensor to direct sampling of values of a physiological parameter by the sensor or request data relating to the physiological parameter from the sensor. In some embodiments, the IMD transmits signals or commands to the sensor by varying an aspect of stimulation delivered to the patient via the conductors. For example, the IMD may vary the number of pacing pulses delivered per cardiac cycle, the amplitude or width of the pacing pulses, or the interval between the pacing pulses. In such embodiments, the sensor includes circuitry to detect delivery of stimulation by the IMD. In some embodiments, the sensor responds by selectively discharging a capacitor on the conductors, or by selectively coupling a load to the conductors during delivery of stimulation. In such embodiments, the IMD includes circuitry to detect the change in voltage on the conductors resulting from discharge of the capacitor, or measure voltage, current, or impedance during delivery of stimulation to detect coupling of the load to the conductors.

In other embodiments, the IMD and the sensor carried by the lead communicate via communication pulses on the conductors according to a more robust communication protocol. For example, in exemplary embodiments, the IMD and sensor communicate by modulating the amplitude or width of communication pulses on the conductors, or by modulating the length of the intervals between communication pulses on the conductors. The communication pulses synchronize a clock maintained by the sensor with a clock maintained by the IMD. In some embodiments, the communication protocol provides defined commands for use by the IMD, and enables addressing of multiple sensors carried by a single lead. In some embodiments in which the IMD comprises a cardiac pacemaker, the IMD and sensor communicate during a refractory period of the patient to avoid unintentional capture of cardiac tissue by the communication pulses. Like the power pulses discussed above, the communication pulses are sub-threshold and, in some embodiments, may be biphasic.

Further, in some embodiments, the IMD temporarily suspends selected functions during at least delivery of power to the sensor or communication with the sensor. The functions are suspended to avoid interference with or from the power delivery and communication on the commonly used conductors. Example functions that may be suspended by the IMD include autocapture detection, lead impedance measurement, battery life estimation, thoracic impedance measurement, minute ventilation measurement, P-wave sensing, R-wave sensing, or T-wave sensing.

In one embodiment, the invention is directed to an implantable medical lead that comprises a first electrode, a second electrode, a first electrical conductor electrically coupled to the first electrode, and a second electrical conductor electrically coupled to the second electrode. The implantable medical lead further comprises a sensor that is coupled across the first and second conductors in parallel with a current path between the first and second electrodes.

In another embodiment, the invention is directed to an implantable medical device system comprising an implantable medical device and an implantable medical lead connected to the implantable medical device. The implantable medical lead comprises a first electrode, a second electrode, a first electrical conductor electrically coupled to the implantable medical device and the first electrode, and a second electrical conductor electrically coupled to the implantable medical device and the second electrode. The implantable medical lead further comprises a sensor coupled across the first and second conductors in parallel with a current path between the first and second electrodes. The implantable medical device delivers stimulation to a patient via the conductors and electrodes, and the sensor receives power from the implantable medical device and communicates with the implantable medical device via the conductors.

In another embodiment, the invention is directed to a method in which an electrical stimulation signal is delivered via an implantable medical lead, and an energy storage element of a sensor carried by the implantable medical lead is charged with the electrical stimulation signal. The lead includes at least one electrode coupled to a conductor, the sensor is coupled to the conductor, and the stimulation signal is delivered via the conductor and the electrode.

In another embodiment, the invention is directed to a method in which an energy storage element of a sensor that is carried by an implantable medical lead is uncoupled from a conductor of the lead during delivery of electrical stimulation from an implantable medical device to a patient via the conductor, and the energy storage element is charged with sub-threshold power pulses delivered by the implantable medical device via the conductor.

In another embodiment, the invention is directed to a method for powering and communicating with a sensor carried by an implantable medical lead that is connected to an implantable medical device, wherein the implantable medical lead includes at least one conductor that is coupled to an electrode and the sensor. The method comprises delivering power from the implantable medical device to the sensor via the conductor, communicating with the sensor via the conductor, and suspending a function of the implantable medical device during at least one of delivery of power to the sensor or communication with the sensor.

In another embodiment, the invention is directed to an implantable medical device that comprises signal generation circuitry and a processor. The signal generation circuitry delivers power to a sensor carried by an implantable medical lead that is connected to the implantable medical device. The implantable medical lead includes at least one conductor that is coupled to an electrode and the sensor, and the signal generation circuitry delivers power to the sensor via the conductor. The processor controls delivery of power by the signal generation circuitry, communicates with the sensor via the conductor, and suspends a function of the implantable medical device during at least one of delivery of power to the sensor or communication with the sensor.

In another embodiment, the invention is directed to a computer-readable medium containing instructions. The instructions cause a programmable processor to control delivery of power from an implantable medical device to a sensor carried by an implantable medical lead via a conductor of the lead that is coupled to an electrode of the lead and the sensor, and communicate with the sensor via the conductor. The instructions further cause the programmable processor to suspend a function of the implantable medical device during at least one of delivery of power to the sensor or communication with the sensor.

In another embodiment, the invention is directed to an implantable medical lead comprising a first electrode, an electrical conductor electrically coupled to the first electrode, and a sensor coupled to the conductor in series with a current path between the first electrode and a second electrode not carried by the lead. The sensor receives power from an implantable medical device and communicates with the implantable medical device via the conductor and the current path, and includes an energy storage element to store power received from the implantable medical device. The implantable medical device at least one of delivers electrical stimulation to a patient or senses electrical activity within the patient via the conductor and the electrode.

The details of one or more embodiments of the invention are set forth in the accompanying drawings and the description below. Other aspects of the invention will be apparent from the description and drawings, and from the claims.

DETAILED DESCRIPTION

Figure 1:
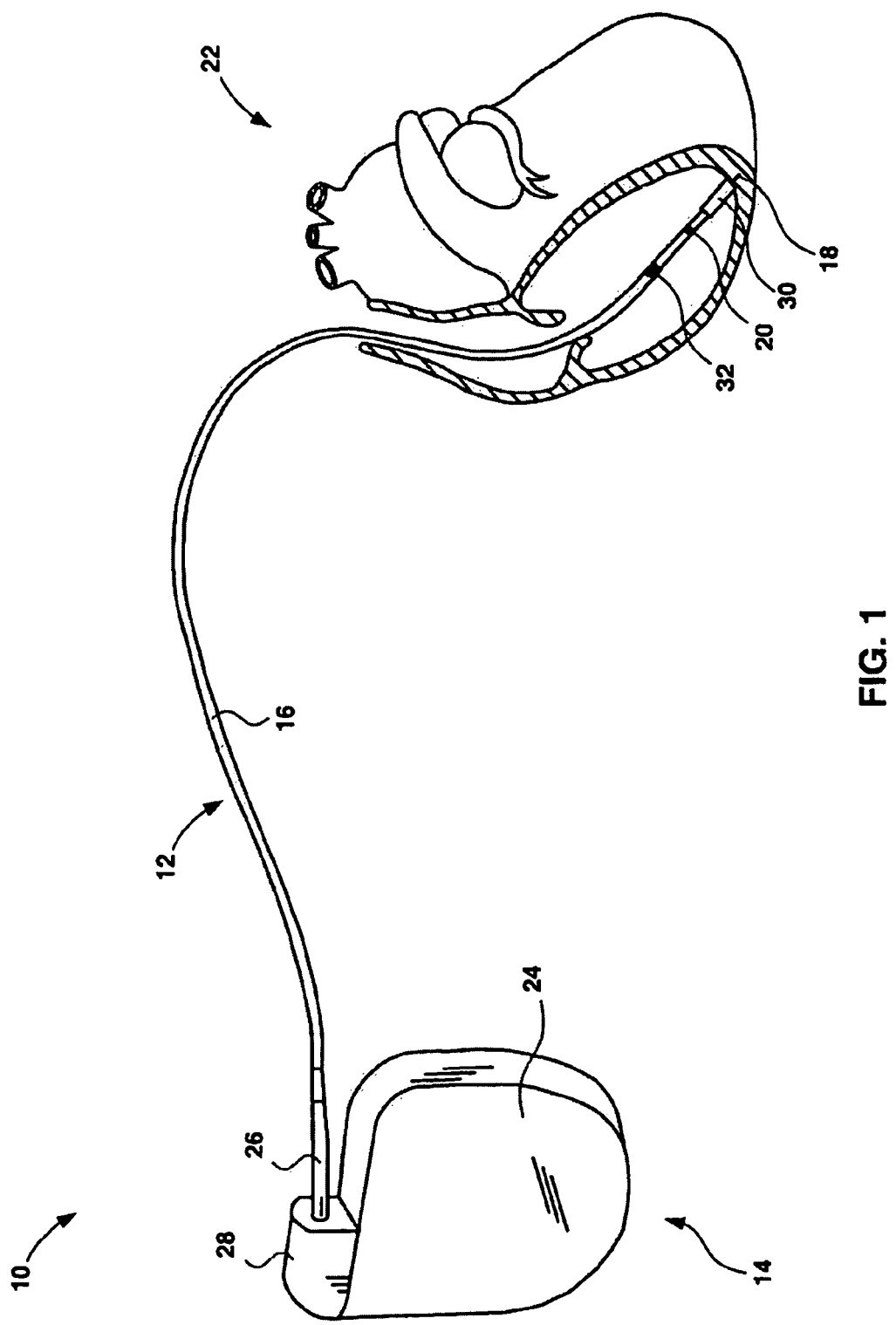
FIG. 1 is a conceptual diagram illustrating an example implantable medical device system including an implantable medical lead that carries a physiological sensor.

FIG. 1 is a conceptual diagram illustrating an example implantable medical device system 10 including an implantable medical lead 12 connected to an IMD 14. As will be described, lead 12 includes a device, such as a physiological sensor, that is coupled to IMD 14 with the same stimulation/sensing conductors used to couple stimulation and sensing electrodes to the IMD. The term "stimulation/sensing sensing" conductor generally refers to a conductor coupled to one or more electrodes to deliver electrical stimulation energy, receive electrical sensing signals, or both.

As shown in FIG. 1, implantable medical lead 12 includes an elongated lead body 16 that carries electrodes 18, 20 at its distal end. IMD 14 delivers electrical stimulation to a patient (not shown) and/or detects electrical activity within the patient via electrodes 18, 20. In particular, in the illustrated embodiment, the distal end of lead body 16 extends into a heart 22 of the patient, and IMD 14 is a cardiac pacemaker that provides bipolar pacing and sensing via tip electrode 18 and ring electrode 20. In other embodiments, IMD 14 provides unipolar pacing and sensing via tip electrode 18 and another electrode not carried by lead body 16, such as an electrode integrated with a housing 24 of IMD 14, i.e., an "active can" electrode.

Lead body 16 also carries conductors (not shown in FIG. 1). In particular, each electrode 18, 20 is coupled to a respective stimulation/sensing sensing conductor that extends through lead body 16, and electrically couples the electrode 18, 20 with circuitry within IMD 14. The circuitry within IMD 14 delivers stimulation and senses electrical activity via the conductors and electrodes 18, 20.

A proximal end of lead body 16 is configured to couple the conductors to the circuitry within IMD 14. For example, in the illustrated embodiment, the proximal end of lead body 16 includes a connector 26 that interfaces with a header 28 of IMD 14 to physically connect lead 12 to IMD 14. Connector 26 and header 28 include electrical contacts to couple the conductors to hermetic feethroughs of housing 24, which in turn couple the conductors to circuitry of IMD 14 within housing 24.

Lead body 16 is made from a biocompatible insulating material, such as polyurethane, ethylene tetrafluoroethylene, silicone, or a polyamide. Electrodes 18, 20 and the stimulation/sensing sensing conductors are made of a biocompatible conductive material, such as platinum or a platinum alloy. In exemplary embodiments, the stimulation/sensing sensing conductors are concentric coiled conductors, arranged co-radially or co-axially, and separated within lead body 16 by tubular insulative sheaths (not shown). In the illustrated embodiment, tip electrode 18 is helical to improve tissue fixation, and housed by a retractable sheath 30. In some embodiments, lead 12 includes one or more tines at or near its distal end to further improve tissue fixation.

Lead 12 also carries a physiological sensor 32, which is an example of device that is coupled to the stimulation/sensing sensing conductors within lead body 16. Sensor 32 receives power from and communicates with IMD 14 via the stimulation/sensing sensing conductors according to the invention. Sensor 32 includes transducer circuitry capable of sensing one or more physiological parameters of the patient, such as oxygen saturation, partial pressure of oxygen, partial pressure of carbon dioxide, temperature, pressure, motion, vibration, glucose or potassium.

In addition to providing power to sensor 32, IMD 14 receives data relating to the physiological parameters from sensor 32 and, in some embodiments, transmits commands to sensor 32 via the stimulation/sensing sensing conductors. In various embodiments, IMD 14 stores the physiological parameter data received from sensor 32 for presentation to a user, such as a clinician. IMD 14 also may analyze the data to identify progression of a disease or symptoms. In some cases, IMD 14 modifies a delivered therapy based on the physiological parameter data. For example, in embodiments in which IMD 14 is a cardiac pacemaker, IMD 14 can control or adjust one or more aspects of the pacing therapy delivered to a patient, such as the aggressiveness of rate responsive pacing, based on the parameter data.

The position of sensor 32 along the length of lead body 18 is merely exemplary. In various embodiments, sensor 32 may be located at any position along lead body 18 suitable for sensing the intended physiological parameter or parameters. Although a single sensor 32 is illustrated in FIG. 1, a lead 12 may include a multiple sensors 32 coupled to the stimulation/sensing sensing conductors. In such embodiments, IMD 14 delivers power to and communicates with the multiple sensors 32 via the stimulation/sensing sensing conductors. In some cases, IMD 14 is capable of addressing individual sensors 32.

In some embodiments, lead 12 includes other electrodes instead of, or in addition to electrodes 18, 20. For example, in some embodiments lead 12 carries one or more defibrillation electrodes (not shown), each of which is coupled to IMD 14 by a conductor within lead body 18 for delivery of cardioversion and/or defibrillation therapy to the patient. Further, in some embodiments, sensor 32 is coupled to one or more conductors that are, in turn, coupled to defibrillation electrodes.

Additionally, the illustrated configuration of implantable medical device system 10 is merely exemplary. For example, in some embodiments the distal end of lead 12 extends to locations within heart 22 other than the right ventricle of heart 22. Further, in some embodiments, an IMD 14 is coupled to a plurality of leads 12, one or more of which carry one or more sensors 32. In such embodiments, the plurality of leads extend to a variety of locations with heart 22.

Moreover, the invention is not limited to embodiments in which IMD 14 is a cardiac pacemaker. For example, in some embodiments, IMD 14 takes the form of a neurostimulator, muscle stimulator, gastric stimulator, or bladder stimulator that is coupled to a lead 12. In this case, lead 12 may include any number of electrodes and a lead body 16 configured in a manner appropriate for delivery of therapy by such an IMD. In each case, a lead 12 coupled to the IMD includes a sensor 32 coupled to one or more stimulation/sensing sensing conductors.

Figure 2:
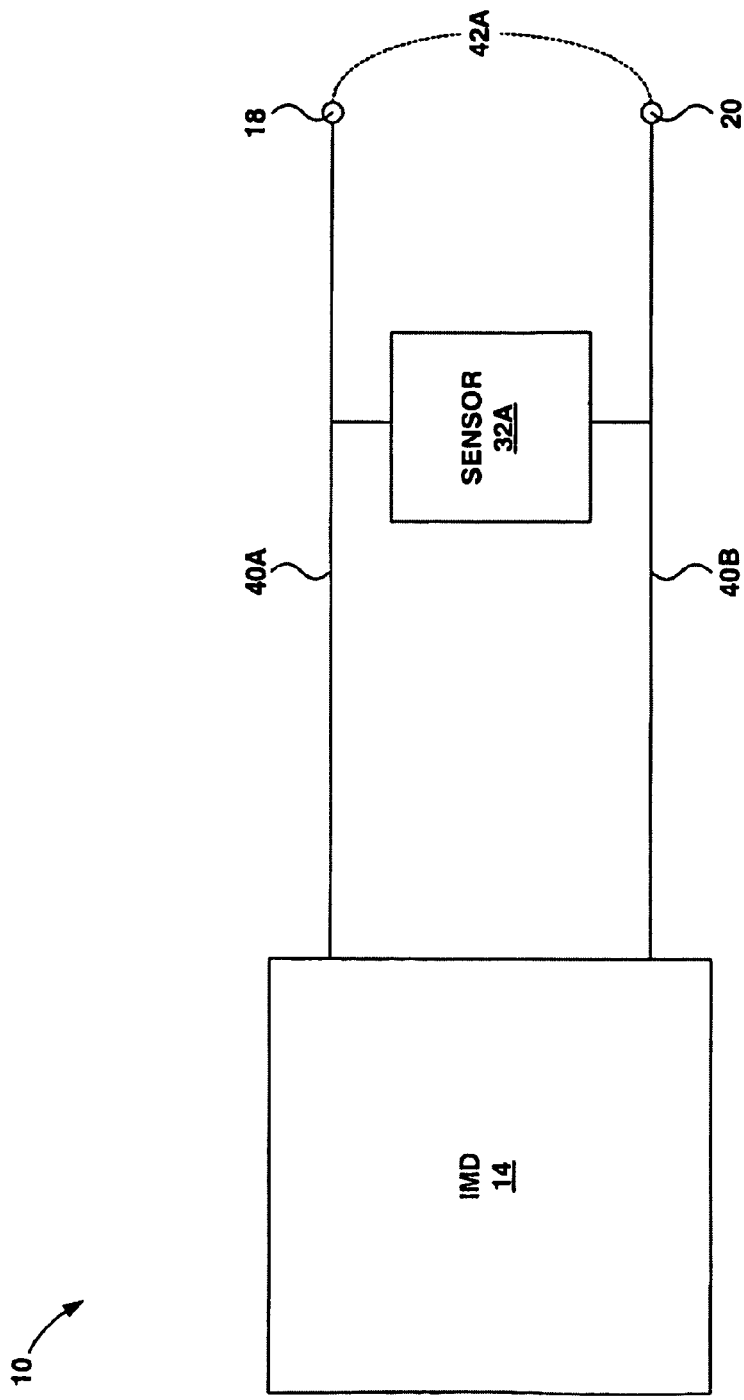
FIG. 2 is a block diagram illustrating a circuit representation of the implantable medical device system of FIG. 1.

FIG. 2 is a block diagram illustrating a circuit representation of implantable medical device system 10. As described above with reference to FIG. 1, electrodes 18, 20 are coupled to IMD 14 by respective stimulation/sensing sensing conductors 40A and 40B (collectively "conductors 40"). In the illustrated embodiment, a sensor 32A is coupled to both of conductors 40 in parallel with a current path 42A between electrodes 18, 20. Current path 42A is the path, between electrodes 18, 20 and through body tissue, along which current travels when stimulation is delivered by IMD 14. To couple sensor 32A to conductors 40 in parallel with current path 42A, sensor 32A is directly coupled to each of electrodes 18, 20 by its respective conductor 40, i.e., with no intervening circuit elements, in accordance with an embodiment of the invention. Consequently, the impedance of each of the paths between sensor 32A and one of electrodes 18, 20 is less than approximately one kOhm, less than approximately 250 Ohm, less than approximately 100 Ohm or, preferably, less than approximately 1 Ohm.

Figure 3A:
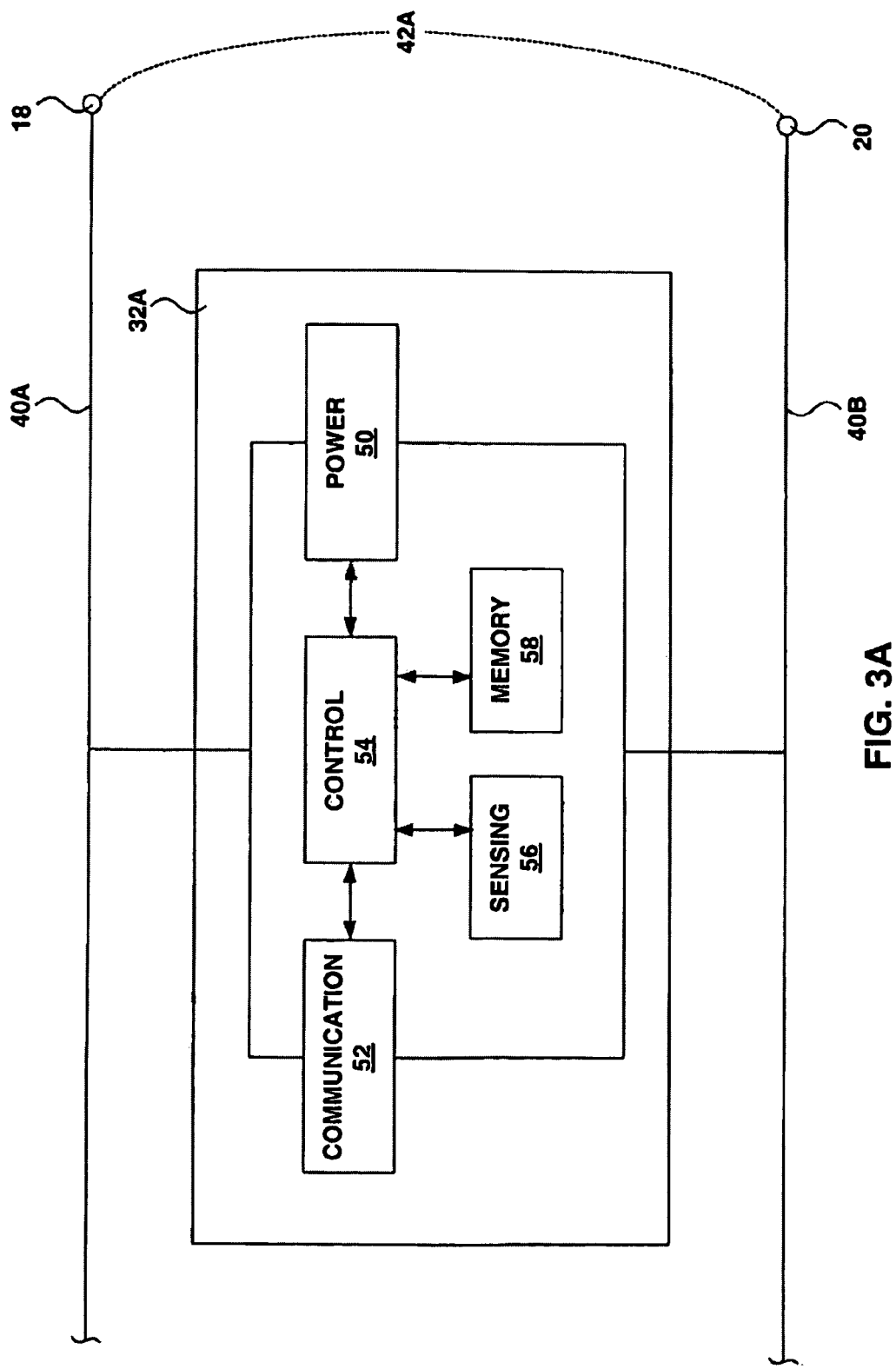
FIG. 3A is a block diagram illustrating the physiological sensor within the circuit representation of FIG. 2.

FIG. 3A is a block diagram further illustrating sensor 32A within the circuit representation of FIG. 2. As illustrated in FIG. 3A, sensor 32A includes a power module 50 and communication module 52, each of which is coupled to conductors 40 in parallel with current path 42A. Sensor 32A also includes a control module 54, sensing module 56 and memory 58.

Power module 50 includes an energy storage element, such as one or more capacitors or a rechargeable battery, to store energy received from IMD 14 via conductors 40. As will be described in greater detail below, the energy storage element is charged by a stimulation waveform, e.g., cardiac pacing pulses, and/or dedicated power pulses delivered by IMD 14 via conductors 40. Power module 50 includes recovery circuitry to recover power from the fluctuating voltages on conductors 40. The recovery circuitry includes circuitry to hold the power received from IMD 14 in the energy storage element in the absence of the waveform or power pulses, such as one or more diodes in series with the energy storage element. In embodiments in which the stimulation and/or power pulses delivered by IMD 14 are AC or biphasic, the recovery circuitry includes circuitry, such as a rectifier circuit, to convert the stimulation and/or power pulses to DC waveforms suitable for charging the energy storage element.

In some embodiments, power module 50 additionally includes circuitry, such as one or more switches, that is responsive to signals from control module 54 to selectively couple and uncouple the energy storage element from one or both of conductors 40. For example, control module 54 can uncouple the energy storage element from conductors 40 during periods in which the energy consumption of sensor 32A is low, such as when sensor 32A is inactive. Sensor 32A is inactive, for example, when it is not communicating with IMD 14 and/or sensing one or more physiological parameters. In such embodiments, control module 54 may recouple the energy storage element to the one or both of conductors 40. For example, recoupling may occur in response to detecting that energy stored in the energy storage element has fallen below a threshold value, or receiving a signal or command from IMD 14 to sense the one or more physiological parameters and/or transmit data relating to the physiological parameters.

In other embodiments, control module 54 selectively uncouples the energy storage element from one or both of conductors 40 during periods in which IMD 14 is delivering stimulation to the patient via conductors 40 and electrodes 18, 20. Control module 54 may uncouple the energy storage element from conductors 40 in response to a signal from IMD 14 indicating an upcoming delivery of stimulation. In such embodiments, control module 54 uncouples the energy storage element from conductors 40 to avoid diversion of a portion of the stimulation energy from the patient to the energy storage element, which may reduce the effectiveness of the stimulation as therapy for the patient. Additionally, with the energy storage element uncoupled from conductors 40, IMD 14 can more accurately measure the amount of stimulation energy delivered to electrodes 18, 20, and the impedance presented to IMD 14 during delivery of stimulation via electrodes 18, 20. These measurements allow IMD 14 to estimate the longevity of its power source, e.g., battery.

Although the connections between power module 50 and the other components 52-58 of sensor 32A are not illustrated in FIG. 3A for the purpose of clarity, power module 50 distributes power from the energy storage element to the other components. In some embodiments, power module 50 includes a voltage regulator circuit to provide appropriate voltages to the other components.

Communication module 52 includes circuitry that allows control module 54 to communicate with IMD 14 via conductors 40. In this manner, control module 54 can detect signals from IMD 14 on conductors 40 and/or place signals on conductors 40 for detection by IMD 14. For example, in some embodiments, communication module 52 includes a capacitor, and control module 54 selectively causes the capacitor to be discharged on conductors 40, e.g., by controlling switches to couple or invert the coupling of the capacitor to conductors 40. In such embodiments, IMD 14 detects the presence or absence of a voltage on conductors 40 associated with discharge of the capacitor during a particular time period, e.g., a bit time, as a data "1" or "0." In other embodiments, communication module 52 includes a load, and control module 54 selectively couples the load to conductors 40 during delivery of stimulation by IMD 14. In such embodiments, IMD 14 measures voltage, current, impedance or a combination thereof during the delivery of stimulation, and detects the presence or absence of the load on conductors 40 during a particular time period, e.g., a bit time, as a data "1" or "0."

In still other embodiments, IMD 14 and control module 54 communicate via communication pulses on conductors 40. In some of these embodiments, a transceiver of communication module 52 includes pulse generation circuitry that is controlled by control module 54 to generate communication pulses with selected amplitudes, durations and polarities. Communication module 52 modulates the amplitude or duration of the pulses, for example, to represent data "1's" or "0's." In other pulse width modulation embodiments, sensor 32A does not itself generate pulses. Instead, the transceiver of communication module 52 includes circuitry to pull down a voltage placed on conductors 40 by IMD 14 at one of two pulse widths to indicate data "1's" or "0's."

Communication module 52 also includes circuitry to detect signals placed on conductors by IMD 14. IMD 14 communicates with sensor 32A by, for example, modulating a parameter of the stimulation delivered to patient, power pulses delivered to sensor 32A, or via communication pulses. In some embodiments, communication module 52 includes sense amplifiers that output a signal to control module 54 when an amplitude of a signal on conductors 40 exceeds a threshold value. Such sense amplifiers may be useful to detect the occurrence of stimulation, such as cardiac pacing pulses, on conductors 40. In other embodiments, a transceiver of communication module 52 receives and decodes communication pulses placed on stimulation/sensing sensing conductors 40 by IMD 14.

Sensing module 56 includes conventional transducer circuitry capable of sensing one or more physiological parameters of the patient, such as oxygen saturation, partial pressure of oxygen, partial pressure of carbon dioxide, temperature, pressure, motion, vibration, glucose or potassium. As one example, in exemplary embodiments in which sensing module 56 senses oxygen saturation, sensing module 56 includes an infrared light emitter and a red light emitter that output light at respective wavelengths, and a single transducer that detects reflected light at the respective wavelengths. Sensing module 56 includes one or more analog to digital converters to convert the analog signals output by transducers to digital signals, which are provided to control module 54.

Control module 54 samples the digital signals, and either controls the communication module 52 to transmit data to IMD 14 indicating the sampled physiological parameter values, or stores sampled values in memory 58 for later transmission to IMD 14. In some embodiments, control module 54 further processes the sampled and stored parameter values to, for example, determine a mean, median, minimum, or maximum value of the physiological parameter that can then be transmitted to IMD 14. In other embodiments, control module 54 processes the sampled and stored parameter values to determine a value of another physiological parameter. In some embodiments, for example, control module 54 processes sampled right ventricular pressure values to determine an estimated pulmonary diastolic pressure value, which may be used by IMD 14 to monitor and/or adjust pacing therapy in response to the progression of congestive heart failure.

In addition to performing the functions described above, control module 54 maintains a clock used by control module 54 to control the timing of physiological parameter sampling by sensing module 56, and communication with IMD 14 by communication module 52. Control module 54 can include a microprocessor, digital signal processor (DSP), application specific integrated circuit (ASIC), field-programmable gate array (FPGA), or other logic circuitry. Memory 58 stores program instructions that, when executed by control module 54, control the function of sensor 32A in the manner described herein. Memory 58 can include read-only memory (ROM), random access memory (RAM), electronically erasable programmable ROM (EEPROM), flash memory, or a combination thereof. In some embodiments, memory 58 includes flash memory, which is capable of retaining stored parameter values or program instructions in the absence of power, e.g., in the event that the energy storage element of power module 50 is temporarily depleted.

In some embodiments, sensor 32A also includes a protection network (not shown) to minimize the effect on sensor 32A of transient voltages and currents occurring on the conductors 40 due to electro-surgery, electro-static discharge, electro-magnetic interference, or delivery of cardioversion or defibrillation pulses. The direct exposure of sensor 32A to some of these voltages through electrodes 18 and body tissue, rather than indirect induction of current or voltages on conductors 40, may require a substantial protection network. The protection network can include, for example, one or more Zener diodes. In embodiments in which sensor 32A is coupled to a conductor 40 that is, in turn, coupled to a defibrillation electrode, the protection network may require a blocking field-effect transistor to protect sensor 32A during delivery of defibrillation or cardioversion therapy via the conductor and the defibrillation electrode.

In some embodiments, it may be desirable to allow lead 12 to be connected to an IMD for stimulation and/or sensing without use of sensor 32A. In such embodiments, power module 50 includes a switch, such as a reed switch that is sensitive to a magnetic field, that is open to disconnect the energy storage element from conductors 40 until receipt of signal, such as placing a magnet or AC driven coil electrode in proximity to the switch. Use of such a switch prevents sensor 32A from consuming power from a power source of IMD 14 or diverting stimulation energy from the patient unless sensor 32A is intended to be used.

In this manner, if physiological sensing is not initially required for treatment of a patient, lead 12 can be implanted and used with sensor 32A inactive. At a later time, when physiological is desired, sensor 32A can be selectively activated. In some cases, an IMD that does not support physiological sensing is initially implanted with the patient and coupled to lead 12. When physiological sensing is later needed, a new IMD that supports physiological sensing is coupled to lead 12 to replace the initial IMD, without requiring that lead 12 be explanted and replaced.

Figure 3B:
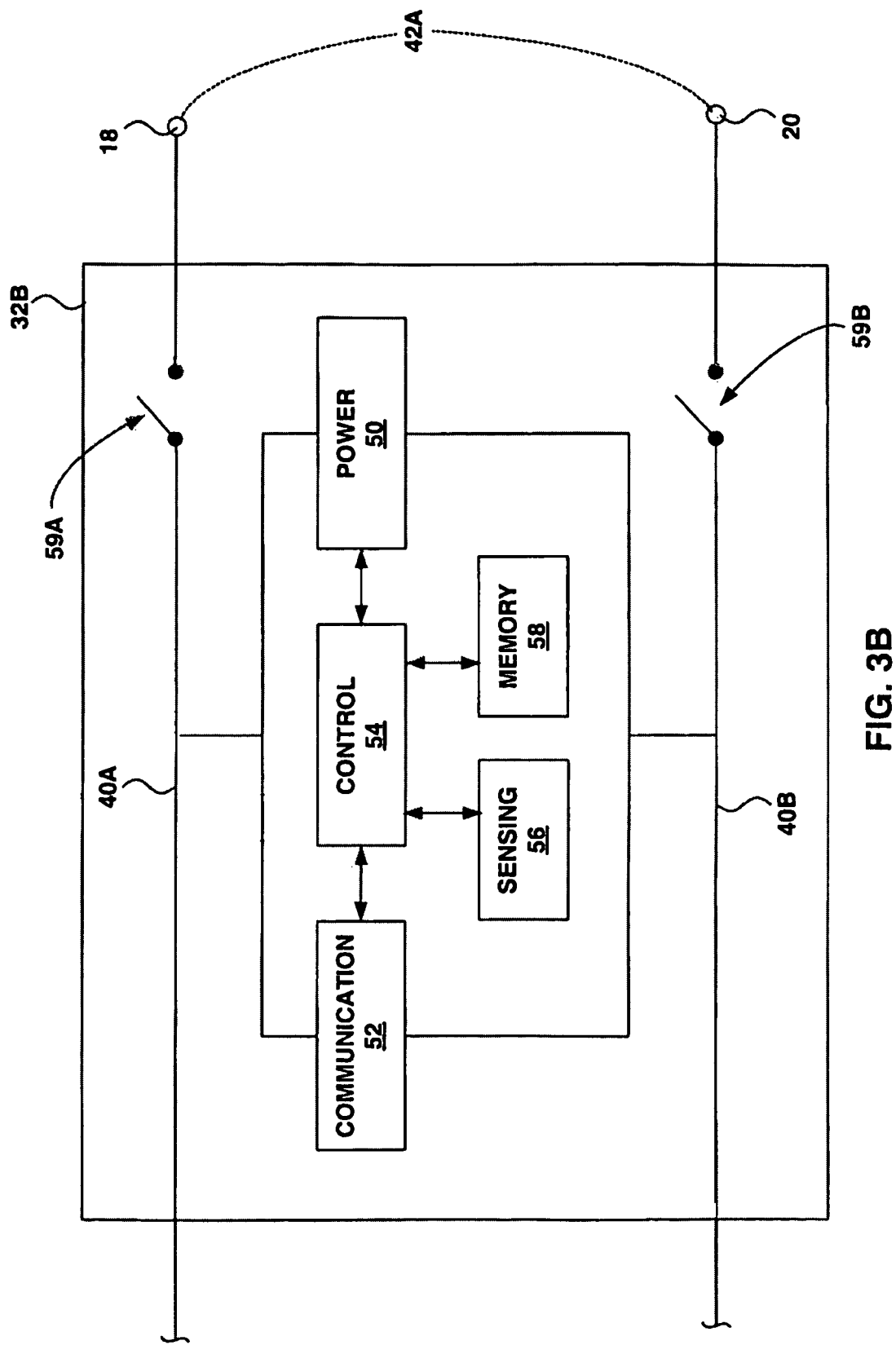
FIG. 3B is a block diagram illustrating another example physiological sensor within the circuit representation of FIG. 2.

FIG. 3B is a block diagram illustrating another example sensor 32B within the circuit representation of FIG. 2. Modules 50-58 of sensor 32B are substantially similar to, and function in substantially the same manner as modules 50-58 of sensor 32A described above with reference to FIG. 3A.

In addition to modules 50-58, and the other components of sensor 32A described above, sensor 32B includes switches 59A and 59B (collectively "switches 59"). The positions of switches 59 are controlled by control module 54 to selectively couple and uncouple electrodes 18, 20 from the remainder of conductors 40A and 40B, respectively. Control module 54 closes switches 59 during delivery of stimulation by IMD 14 to allow the stimulation to traverse the current path 42A between electrode 18 and 20, i.e., to allow the stimulation to be delivered to a patient. Control module 54 opens switches 59 during periods between delivery of stimulation by IMD 14 to remove electrodes 18, 20 and current path 42A from the circuit that includes IMD 14 and sensor 32B. Control module 54 can, for example, open switches 59 for a predetermined period of time after communication module 52 detects delivery of stimulation by IMD 14 on conductors 40, or can open and close switches 59 in response to signals that communication module 52 receives from IMD 14 on conductors 40.

IMD 14 can deliver power to and communicate with sensor 32B during the periods between delivery of stimulation to the patient. With switches 59 open, power and communication signals placed on conductors 40 by IMD 14 and sensor 32B do not traverse current path 42A and, therefore, cannot inappropriately stimulate the tissue of the patient. Additionally, with switches 59 open, the current drain associated with delivery of power to and communication with sensor 32B is reduced by removal of the parallel load presented by current path 42A from the circuit that includes IMD 14 and sensor 32B.

Because sensor 32B includes switches 59, the connections between IMD 14 and electrodes 18, 20 are not mechanically continuous. Accordingly, such embodiments may be less desirable than those in which a sensor 32A is configured as illustrated by FIG. 3A. In some embodiments, a sensor 32 includes only a single switch 59 on one of conductors 40 which, when open, substantially reduces both inappropriate stimulation of patient tissues by power and communication signals, and current drain.

Figure 4:
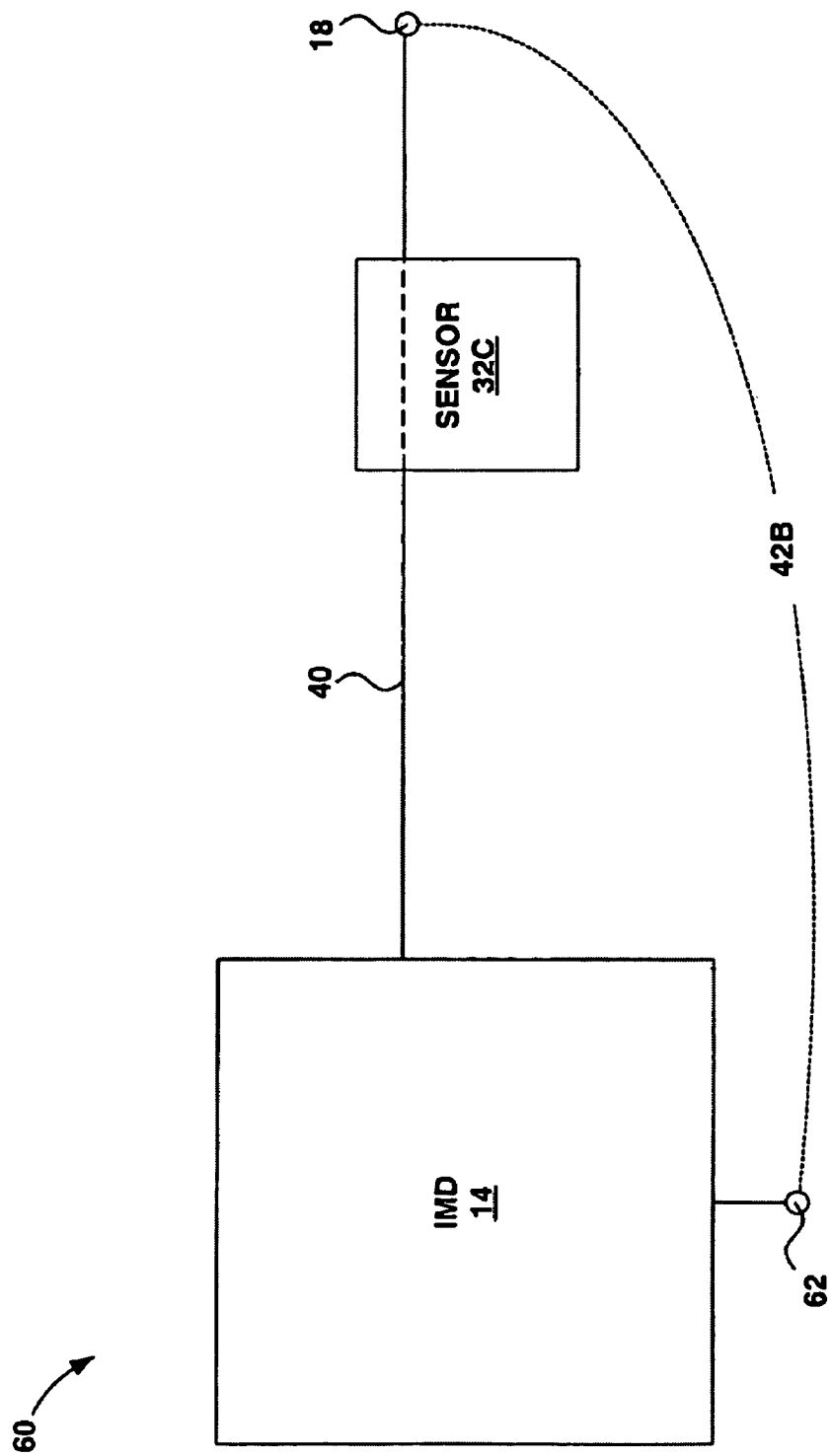
FIG. 4 is a block diagram illustrating a circuit representation of another example implantable medical device system.

FIG. 4 is a block diagram illustrating a circuit representation of another example implantable medical device system 60. As illustrated by the circuit representation, in this embodiment, lead 12 (FIG. 1) includes a single electrode 18 coupled to IMD 14 by a single stimulation/sensing sensing conductor 40. In embodiments in which IMD 14 is cardiac pacemaker, such a lead is used for unipolar pacing and sensing, with stimulation current flowing through a current path 42B between electrode 18 and an additional electrode 62 that is not carried by lead 12. In exemplary embodiments, electrode 62 is integrated with housing 24 (FIG. 1) of IMD 14. In the illustrated embodiment, a sensor 32C is coupled to conductor 40 in series with current path 42B.

Figure 5:
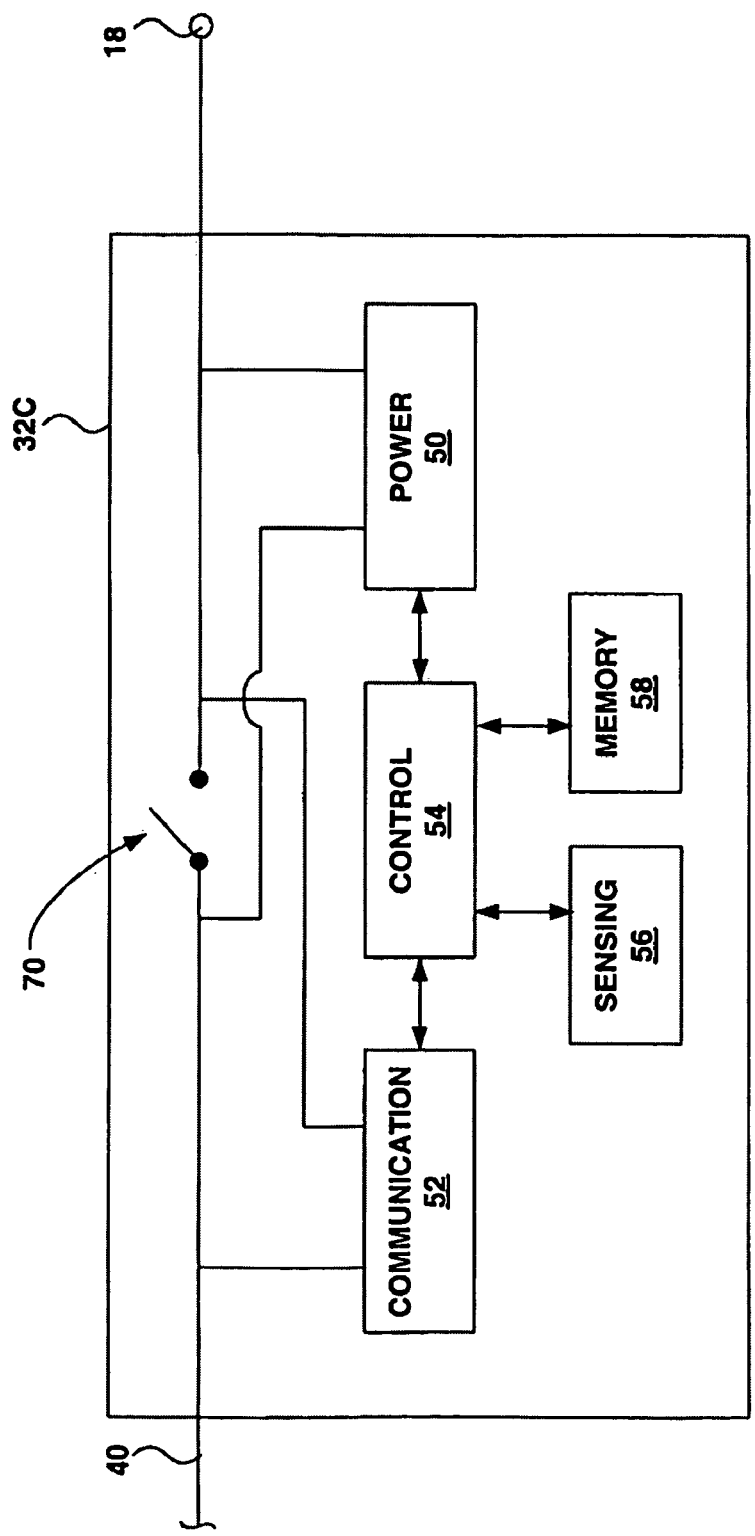
FIG. 5 is a block diagram illustrating another example physiological sensor carried by an implantable medical lead within the circuit representation of FIG. 4.

FIG. 5 is a block diagram illustrating sensor 32C within the circuit representation of FIG. 4. Modules 50-58 of sensor 32C are substantially similar to, and function in substantially the same manner as modules 50-58 of sensor 32A described above with reference to FIG. 3A.

In addition to modules 50-58, and the other components of sensor 32A described above, sensor 32C includes a switch 70, the position of which is controlled by control module 54 to selectively couple and uncouple two portions of conductor 40. When switch 70 is closed, stimulation and other signals from IMD 14 traverse conductor 40, electrode 18, and the return current path 42B to IMD 14 via electrode 62. Control module 54 can open switch 70 during periods between delivery of stimulation by IMD 14. Opening switch 70 provides a "two-wire" bus, one of the wires including current path 42B, between IMD 14 and both of power module 50 and communication module 54.

With switch 70 open IMD 14 can deliver power pulses to sensor 32C via this "two wire bus. Further, IMD 14 and sensor 32C communicate via this "two-wire" bus via, for example, selective coupling of a capacitor to the portions of conductor 40 or communication pulses on the portions of conductor 40 in the manner described above with reference to sensor 32A and conductors 40A and 40B. Because sensor 32C includes switch 70, the connection between IMD 14 and electrode 18 is not mechanically continuous. Accordingly, embodiments in which an implantable medical device system 60 is configured as illustrated in FIGS. 4 and 5 may be less desirable than those in which an implantable medical device system 10 is configured as illustrated by FIGS. 2 and 3A.

Figure 6:
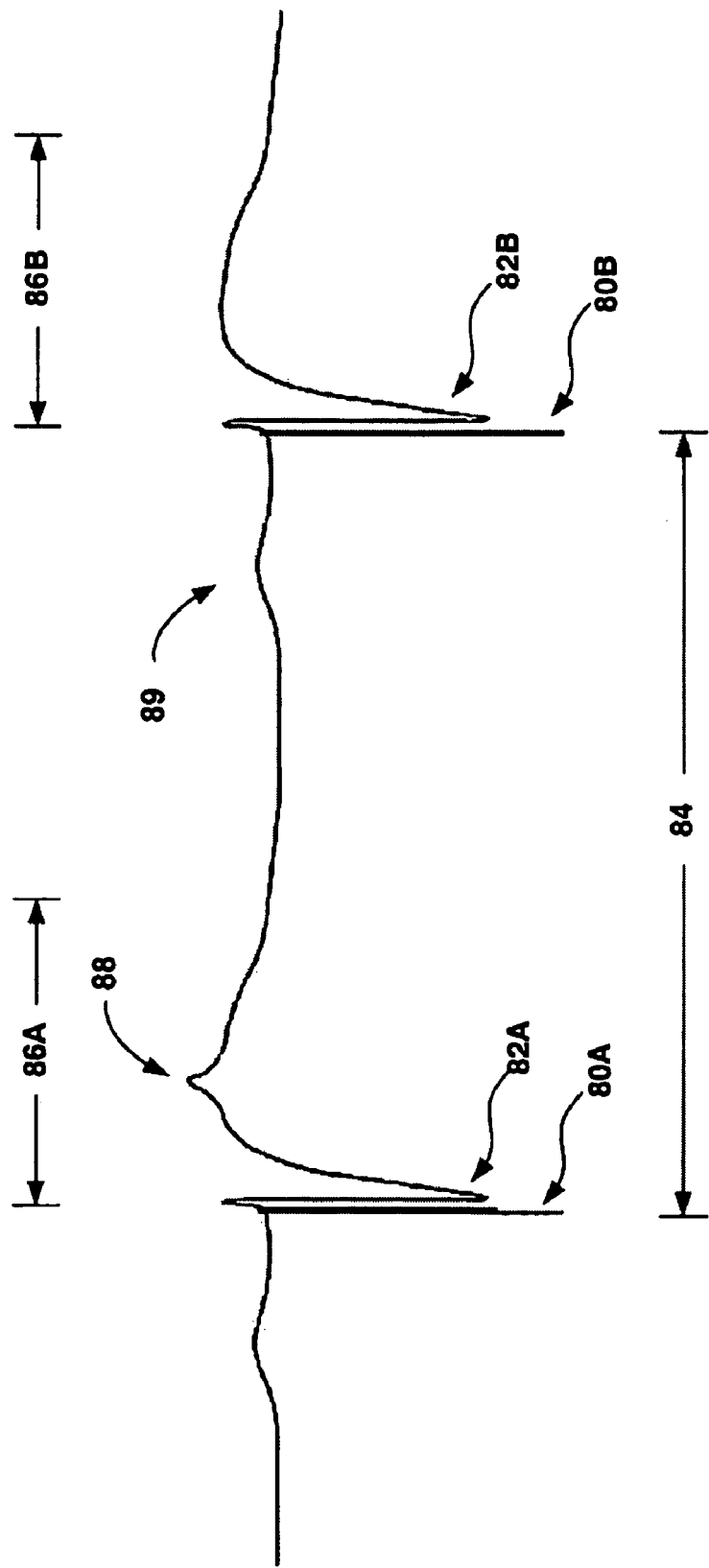
FIG. 6 is a timing diagram illustrating a cardiac electrogram and an example method for transmission of data from a physiological sensor to an implantable medical device according to an example embodiment of the invention.

FIG. 6 is a timing diagram illustrating a cardiac electrogram. The electrogram represents the voltage present between electrodes 18, 20 or 18, 62, as detected by IMD 14 via one or more stimulation/sensing sensing conductors 40. According to the illustrated embodiment, IMD 14 takes the form of a cardiac pacemaker that delivers cardiac pacing pulses 80A and 80B (collectively "pacing pulses 80") to cardiac tissue of a heart 22 of a patient via electrodes 18, 20 or 18, 62. Pacing pulses 80 and the resulting depolarizations 82A and 82B (collectively "depolarizations 82") of the surrounding tissue are depicted within the cardiac electrogram of FIG. 6.

In some embodiments, pacing pulses 80 charge an energy storage element of a sensor 32. Further, in some embodiments IMD 14 communicates with sensor 32, e.g., sends a signal or command to sensor 32, by altering or modulating some parameter of pacing pulses 80. For example, IMD 14 may vary the amplitude or width of pacing pulses 80, or may vary the length of an interval 84 between pacing pulses 80. IMD 14 may vary the length of interval 84 by a small amount of time relative to a programmed escape interval for delivery of pacing pulse 80, such as ten milliseconds. In other embodiments, IMD 14 delivers two or more pacing pulses 80 in rapid succession. A first pacing pulse captures the surrounding tissue of heart 22, while the other pacing pulses occur during a refractory period 86A or 86B (collectively "refractory periods 86") after the resulting depolarization 82 of the surrounding tissue. By varying interval 84 by a relatively small amount of time, or delivering additional pacing pulses 80 during the refractory period 86, IMD 14 is able to provide signals or commands to sensor 32 via stimulation/sensing sensing conductors 40 without compromising the delivery of therapy via the conductors.

As discussed above, communication module 52 is able to detect cardiac pacing pulses 80 on conductors 40, and indicate the occurrence of pacing pulses 80 to control module 54. In order to receive signals or commands from IMD 14, control module 54 measures the time between signals received from communication module 52 that represent the occurrence of pacing pulses 80. In some cases, sensor 32 detects the occurrence of "long" or "short" intervals 84, or multiple pacing pulses 80 within a single cardiac cycle as signal or command. In other cases, sensor 32 detects a pattern of "long" or "short" intervals 84, or the number of pacing pulses 80 per cardiac cycle over a plurality of cardiac cycles as a signal or command. For example, IMD 14 sends signals or commands to sensor 32 to cause sensor 32 to sample physiological parameter values and/or transmit measured values to IMD 14.

The electrogram of FIG. 6 also illustrates a method that is employed by sensor 32 to transmit data to IMD 14 according to some embodiments of the invention. In particular, FIG. 6 illustrates transmission of data to IMD 14 by selectively coupling a capacitor to conductors 40, as described above with reference to sensor 32A and FIG. 3. Selectively coupling a capacitor to conductors 40 results in a voltage signal 88 on conductors 40. IMD 14 detects the presence or absence of a voltage signal 88 during a defined time period, e.g., a bit time, as a data "1" or "0." In some embodiments, the time period is as long as a cardiac cycle, i.e., sensor 32 transmits a single bit of data to IMD 14 per cardiac cycle. In certain embodiments, sensor 32 transmits data to IMD 14 shortly after stimulation, so as to actively provide charge balancing at the electrode, or during refractory periods 86, so that voltage signals 88 are incapable of inadvertently stimulating the patient, e.g., capturing the surrounding tissues of heart 22. In some embodiments, sensor 32 transmits data during refractory periods 86 prior to the occurrence of a T-wave 89.

Figure 7:
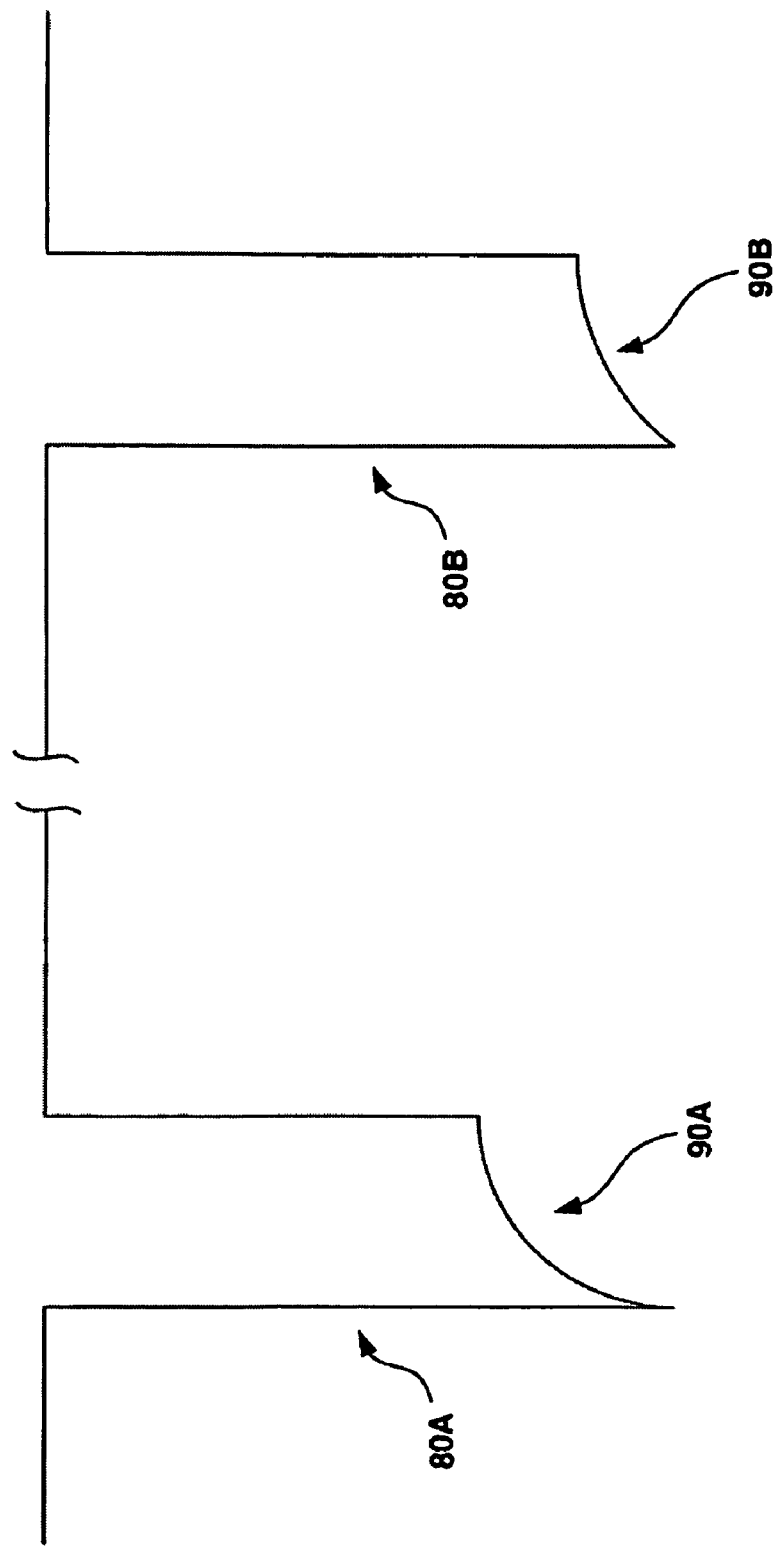
FIG. 7 is a timing diagram illustrating example cardiac pacing pulses and an example method for transmission of data from a physiological sensor to an implantable medical device according to another example embodiment of the invention.

FIG. 7 is a timing diagram illustrating example cardiac pacing pulses 80, and an example method for transmission of data from a sensor 32 to IMD 14 according to another embodiment of the invention. In some embodiments, as described above, sensor 32 transmits data to IMD 14 by selectively coupling a load to, e.g., across, one or more conductors 40 during delivery of stimulation by IMD 14 via the conductors. FIG. 7 illustrates an example method that can be employed by sensor 32 to transmit data to IMD 14 by selectively coupling a load across conductors 40 during delivery of pacing pulses 80 via the conductors.

IMD 14 detects whether sensor 32 has coupled the load across conductors 40 by measuring voltage, current, or impedance during delivery of pacing pulses 80. In some embodiments, IMD 14 measures both voltage and current during delivery of pacing pulses 80, and determines the impedance based on the measured voltage and current values. In other embodiments, IMD 14 measures voltage and current during delivery of pacing pulses 80 to detect changes in the impedance based on changes in the measured voltage and current.

For example, in exemplary embodiments, IMD 14 measures the voltage or current decays 90A and 90B (collectively "decays 90") during delivery of cardiac pacing pulses 80A and 80B, respectively. In the illustrated example, sensor 32 couples the load across conductors 40 during delivery of pacing pulse 80A, resulting in lower impedance and larger decay 90A. Sensor 32 does not couple the load across conductors 40 during delivery of pacing pulse 80B, resulting in higher impedance and a smaller decay 90B. IMD 14 interprets larger decays 90A and smaller decays 90B as data "1's" and "0's" using, for example, a threshold decay value to distinguish between larger decays 90A and smaller decays 90B.

Figure 8:
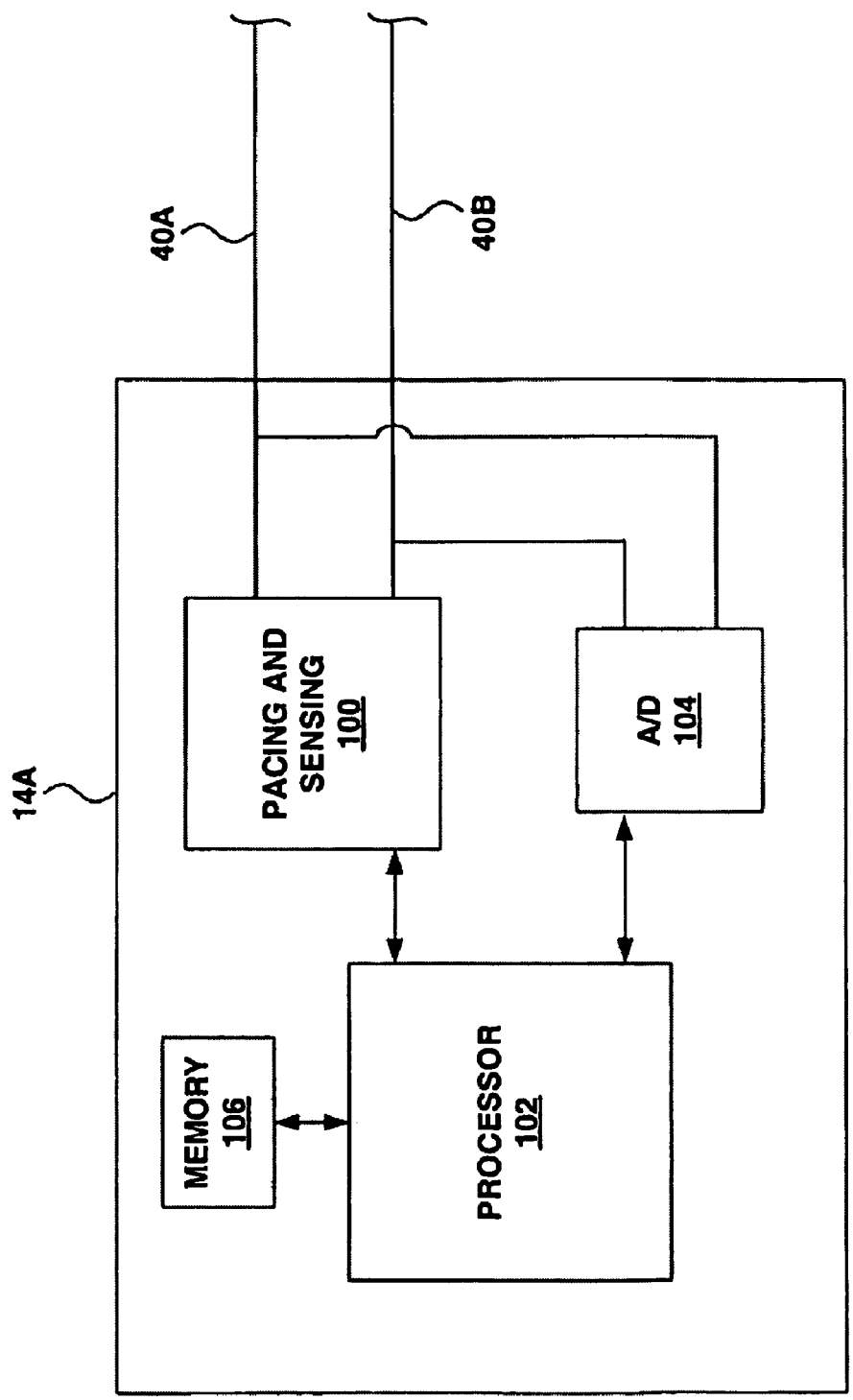
FIG. 8 is a block diagram illustrating an example implantable medical device.

FIG. 8 is a block diagram illustrating an example IMD 14A. IMD 14A includes a pacing and sensing module 100 coupled to conductors 40. Pacing and sensing module 100 includes circuitry for use in generation of stimulation signals, such as cardiac pacing pulses 80, and detection of electrical activity of heart 22, such as depolarizations 82. Pacing and sensing module 100 also maintains counters to control the timing of delivery of pacing pulses 80, e.g., escape interval counters, as is known in the art. In some embodiments, pacing and sensing module 100 also includes circuitry for measuring impedance, such as for battery life, lead impedance, thoracic impedance, or minute ventilation monitoring.

Further, in some embodiments, IMD 14A includes additional modules and circuitry that provide additional therapy delivery or sensing capabilities, such as an accelerometer, or circuitry to detect cardiac arrhythmias and provide cardioversion or defibrillation therapy. Moreover, as indicated above, the invention is not limited to embodiments in which an IMD takes the form of a cardiac pacemaker with a pacing and sensing module 100. In various embodiments, an IMD additionally or alternatively includes modules and circuitry known in the art for providing neurological, muscular, gastrological, or urological stimulation and/or sensing. Like sensor 32A described above, IMD 14A can also include a protection network (not shown) to minimize the effect on IMD 14A of transient voltages and currents occurring on the conductors 40 due to electro-surgery, electro-static discharge, electro-magnetic interference, or delivery of cardioversion or defibrillation pulses.

IMD 14A also includes a processor 102. Processor 102 controls the sensing and delivery of therapy by pacing and sensing module 100 by, for example, setting or adjusting various interval counters, and setting the sensitivity of the circuitry used to sense electrical activity of heart 22. Processor 102 also communicates with sensor 32 via conductors 40 using any of the methods described herein. For example, processor 102 can vary intervals 84 between pacing pulses 80 by changing the value of one or more of the interval counters.

Processor 102 also receives data from sensor 32 via conductors 40 using any of the methods described herein. In some embodiments, for example, pacing and sensing module 100 measures at least one of voltage, current, or impedance during delivery of pacing pulses 80, and provides the measured values to processor 102. Processor 102 identifies data "1's" and "0's" transmitted by sensor 32 by coupling a load to conductors based on the voltage, current, or impedance values measured by the pacing and sensing module 100. In other embodiments, processor 102 processes an electrogram signal received via conductors 40 to detect whether sensor 32 has coupled a capacitor to the conductors, causing signal 88.

An analog to digital converter (A/D) 104 is coupled to conductors 40 in parallel with pacing and sensing module 100, and converts the analog electrogram signal on conductors 40 to a digital signal for processing by processor 102. Processor 102 processes the digital electrogram signal to identify a voltage change associated with coupling of the capacitor to conductors 40. In some embodiments, for example, processor 102 filters the digital electrogram signal, and identifies rapid voltage changes associated with discharge of the capacitor on conductors 40.

By digitally processing the electrogram signal, rather than detecting signals 88 via analog sensing circuitry of IMD 14A, processor 102 can detect signals 88 that occur during a blanking period of the analog sensing circuitry. In exemplary embodiments, processor 102 includes a DSP to process the digital electrogram signal, and can include any a microprocessor, DSP, ASIC, FPGA, or other digital logic circuitry. Processor 102 maintains a clock that controls the timing of the various functions provided by IMD 14A as described herein and, for example, is used by processor 102 to define a bit time during which a determination of whether or not sensor 32 has coupled the capacitor to conductors 40 is interpreted as a data "1" or "0."

In some embodiments, processor 102 stores the physiological parameter data received from sensor 32 in a memory 106 for later retrieval by a clinician via a telemetry module (not shown). In other embodiments, processor 102 monitors the state or progression of a disease or symptom based on the values, and indicates the same to the clinician via the telemetry module. In exemplary embodiments, processor 102 controls or modifies sensing or delivery of therapy by a sensing and therapy delivery module based on the physiological parameter data. In some embodiments, processor 102 modifies one or more interval counters maintained by pacing and sensing module 100, or the aggressiveness of rate responsive pacing therapy provided by pacing and sensing module 100, based on the physiological parameter data received from sensor 32.

During delivery of power to sensor 32 and communication with sensor 32, processor 102 may temporarily suspend one or more other functions of IMD 14A to avoid interference between those functions and the power delivery and communication. In some embodiments, for example, IMD 14A suspends impedance measurement related functions, such as lead impedance measurement, battery life estimation, thoracic impedance measurement, or minute ventilation measurement. In other embodiments, IMD 14A suspends voltage measurement related functions, such as P-wave sensing, R-wave sensing, or T-wave sensing. The methods described herein for communication between sensor 32 and IMD 14A via conductors 40 could affect the accuracy of an impedance or voltage measurement made via the conductors. Further, some impedance measurement functions involve delivery of a current via conductors 40, which could interfere with the accuracy of communication between IMD 14A and sensor 32.

Additionally, in some embodiments in which an energy storage element of sensor 32 charged by the stimulation signal, e.g., cardiac pacing pulses 80, delivered by pacing and sensing module 100, processor 102 suspends autocapture functions, e.g., threshold testing, during periods in which the energy storage element is charged. Typically, autocapture involves periodically adjusting the amplitude of pacing pulses 80, and monitoring the electrogram to detect whether pacing pulses 80 captured surrounding tissues of heart 22, i.e., resulted in a depolarization 82. The result of an autocapture routine is maintenance of the pacing pulse amplitude at a steady-state value that is as low as possible while still reliably capturing the surrounding tissues in order to conserve the power of a power source, e.g., battery, of IMD 14A that provides power for components 100-106 and sensor 32.

The varying load presented by sensor 32 may make it difficult for an autocapture routine to maintain a steady-state pacing amplitude, particularly during periods in which sensor is active. During those periods, the energy storage element is coupled to conductors 40, and sensor 32 is sampling physiological parameter values, and/or sensor 32 is transmitting data to IMD 14A. Consequently, in some embodiments, processor 102 suspends autocapture functions during such periods.

Further, in some embodiments, processor 102 increases the amplitude of pacing pulses 80 during such periods. In other embodiments, sensor 32 is active substantially continuously or, in any event, presents a substantially constant load to IMD 14A. In such embodiments, processor 102 may execute the autocapture routine to maintain a steady-state pacing amplitude that provides adequate stimulation energy to both capture surrounding tissues and charge the energy storage element of sensor 32.

In some embodiments, one or more functions of IMD 14A can be performed periodically. In such embodiments, processor 102 can provide a signal sensor 32 to disable the sensor during performance of the function, rather than suspending the functions during communication or powering of sensor 32. For example, processor 102 can signal sensor 32 to uncouple its energy storage element from conductors 40 during periodic performance of autocapture functions, e.g., stimulation threshold detection.

As indicated above, processor 102 in some embodiments stores data received from sensor 32 in memory 106. Further, in some embodiments, memory 106 stores program instructions that, when executed by processor 102, cause IMD 14A to provide the functionality described herein. Memory 106 can include any one or more of a ROM, RAM, EEPROM, or flash memory.

Figure 9:
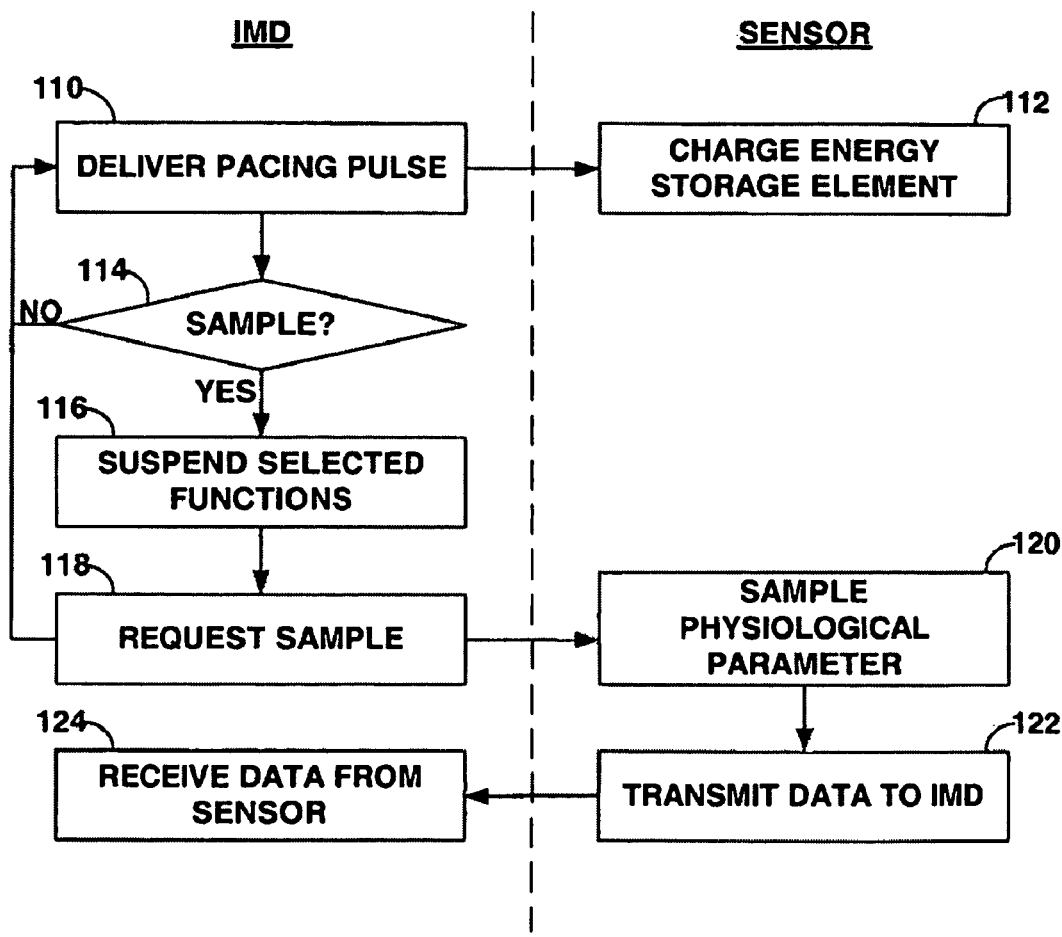
FIG. 9 is a flow diagram illustrating delivery of power from an implantable medical device to a physiological sensor and communication between the implantable medical device and the sensor according to an example embodiment of the invention.

FIG. 9 is a flow diagram illustrating delivery of power from IMD 14A to sensor 32, and communication between IMD 14A and sensor 32 according to an example embodiment of the invention. According to the example method, IMD 14A delivers cardiac pacing pulses 80 to a patient via one or more conductors 40 and electrodes 18, 20 or 18, 62 (110). In addition to stimulating heart 22, the pacing pulses 80 charge an energy storage element of sensor 32 that is coupled to the one or more conductors 40 (112).

When IMD 14A determines that it requires updated data regarding a physiological parameter (114), IMD 14A temporarily suspends one or more selected functions, such as the impedance or voltage measurement related functions identified above, in anticipation of upcoming communication with sensor 32 (116). In some embodiments, IMD 14A additionally or alternatively temporarily suspends autocapture functions and increases the amplitude of pacing pulses 80 in anticipation of an increased or more variable consumption of energy from pacing pulses 80 by sensor 32 during sampling and communication with IMD 14A. IMD 14A determines that it requires updated data according to a schedule stored in memory 106, for example.

IMD 14A then transmits a signal or command to sensor 32 by, for example, varying the interval 84 between pacing pulses 80, or delivering multiple pacing pulses 80 during a single cardiac cycle, to request that sensor 32 samples the physiological parameter (118). Sensor 32 detects pacing pulses 80, measures intervals 84 between pacing pulses 80, and receives the signal from IMD 14A communicated via pacing pulses 80. In response to receipt of the signal, sensor 32 samples one or more physiological parameters (120), and transmits data relating to the sampled physiological parameters to IMD 14A (122). As discussed above, sensor 32 transmits data to IMD 14A by, for example, selectively coupling a capacitor or load to conductors 40. After IMD 14A has received the data from sensor 32 (124), IMD 14A resumes suspended functions and, in some embodiments, reduces the amplitude of pacing pulses 80 to the value in use prior to requesting sampling by sensor 32.

The invention is not, however, limited to the example method illustrated in FIG. 9. In some embodiments, for example, the energy storage element of sensor 32 is uncoupled from conductors 40 prior to sensor 32 receiving a signal from IMD 14. In other embodiments, sensor 32 samples the physiological parameter substantially continuously, or periodically based on a schedule. In such embodiments, sensor 32 updates, for example, a mean or median value of the physiological parameter based on the samples, and transmits the mean or median value to IMD 14A upon receiving a request from IMD 14A. Further, sensor 32 need not receive requests from IMD 14A, and can sample physiological parameter values and transmit data to IMD 14A autonomously in a substantially continuous manner, or based on a schedule stored in memory 58.

Figure 10:
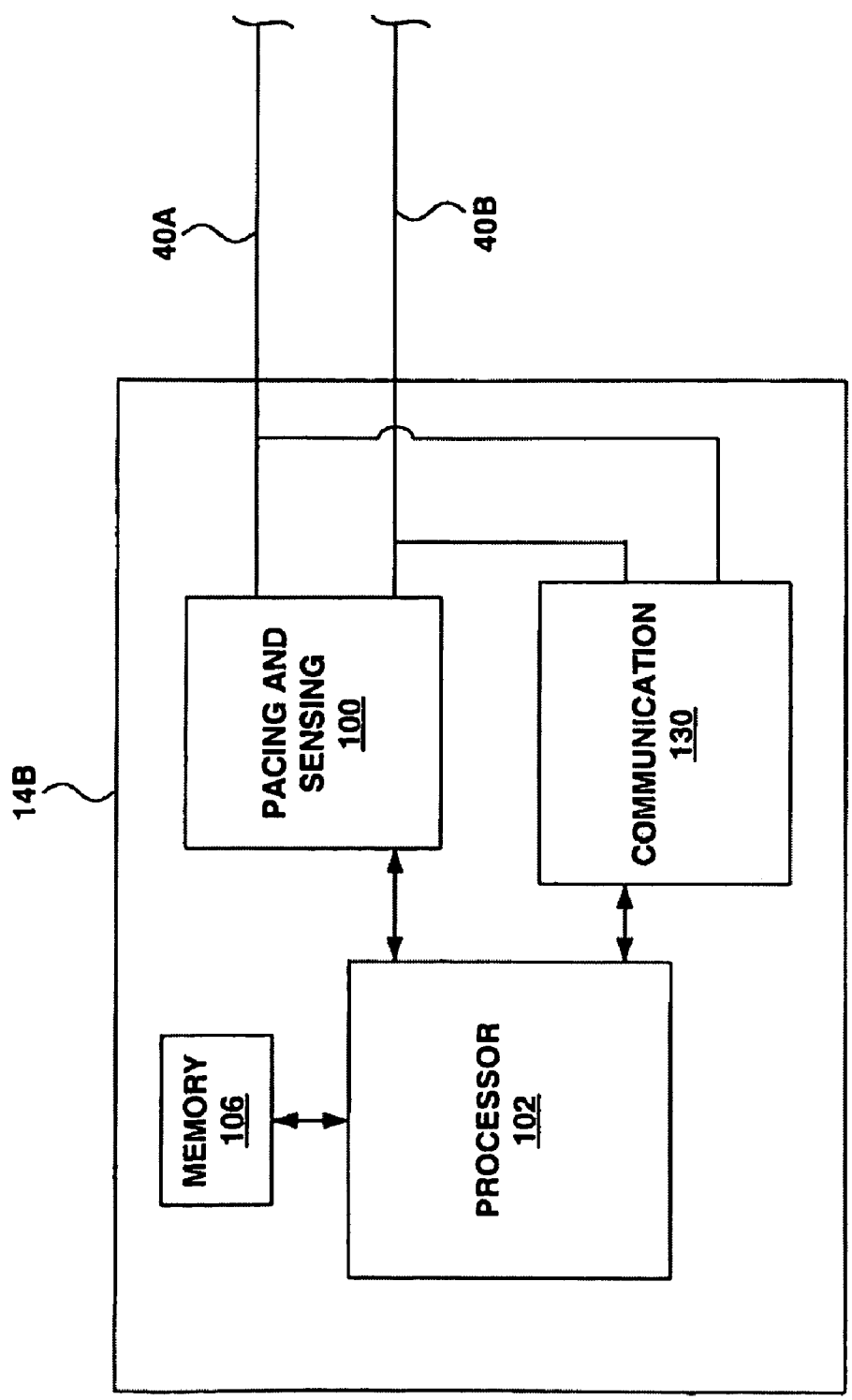
FIG. 10 is a block diagram illustrating another example implantable medical device.

FIG. 10 is a block diagram illustrating another example implantable medical device 14B. Like IMD 14A depicted in FIG. 8, IMD 14B includes a pacing and sensing module 100 coupled to conductors 40, a processor 102, and a memory 106. However, rather than A/D 104, IMD 14B includes a communication module 130 coupled to conductors 40 in parallel with pacing and sensor module 100. Communication module 130 includes a transceiver that allows processor 102 to communicate with sensor 32 via communication pulses on conductors 40. In exemplary embodiments, IMD 14B does not provide power to sensor 32 via pacing pulses 80, and communication module 130 includes signal generation circuitry for generation of both communication pulses and power pulses on conductors 40.

Figure 11:
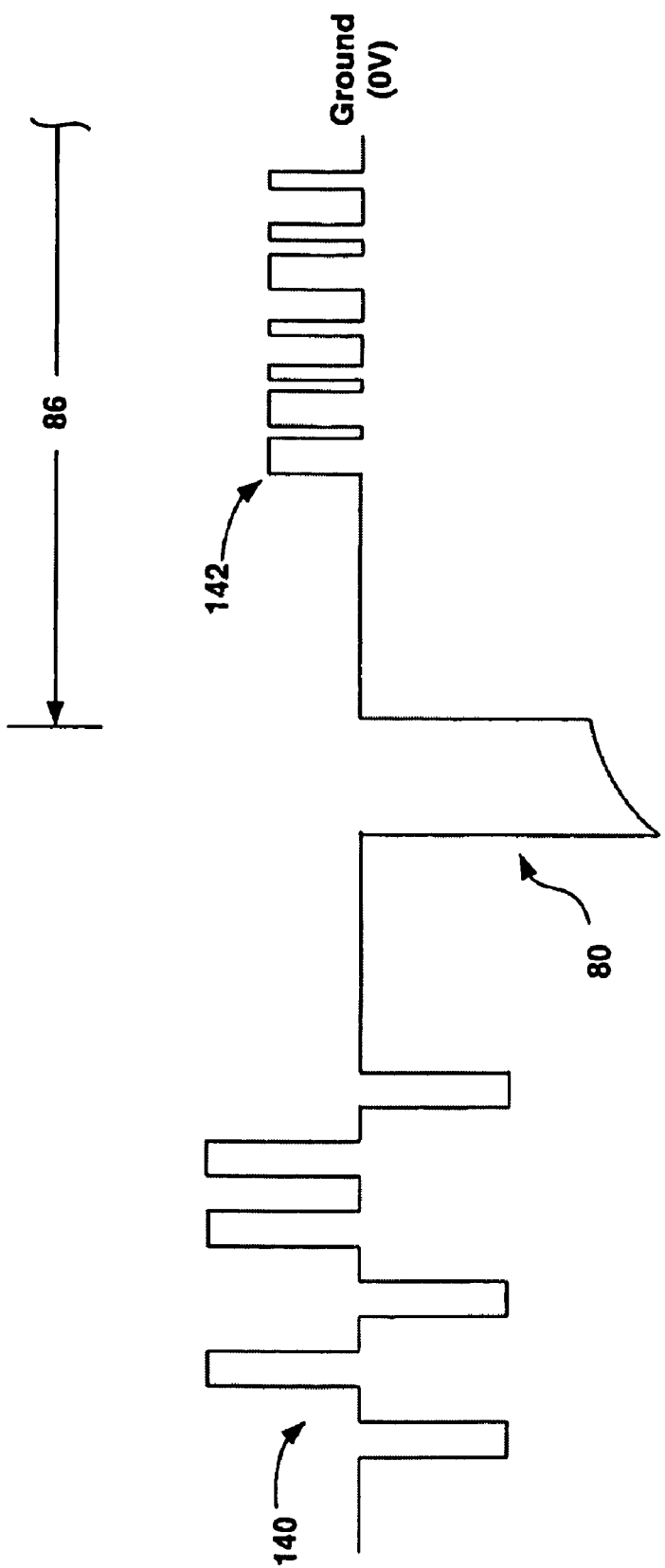
FIG. 11 is a timing diagram illustrating delivery of power from an implantable medical device to a physiological sensor and communication between the implantable medical device and the sensor according to another example embodiment of the invention.

FIG. 11 is a timing diagram illustrating delivery of power from IMD 14B to sensor 32 and communication between IMD 14B and sensor 32 via conductors 40. As shown in FIG. 11, IMD 14B delivers power to sensor 32 via power pulses 140, which charge the energy storage element of sensor 32. In exemplary embodiments, as illustrated in FIG. 11, IMD 14B delivers power pulses 140 that are biphasic pulse pairs to avoid charge build up at electrodes 18, 20 coupled to conductors 40. In such embodiments, power module 50 of sensor 32 includes a rectifier circuit to allow the energy storage element to recover the charge from biphasic power pulse pairs 140. IMD 14B, and in some embodiments sensor 32, also place communication pulses 142 on conductors 40 for the purpose of bidirectional communication between IMD 14B and sensor 32. Although illustrated in FIG. 11 as unipolar pulses, communication pulses 142 can also take the form of biphasic pulse pairs to avoid charge build up at electrodes 18, 20 coupled to conductors 40. In various embodiments, power pulses 140 and communication pulses 142 are voltage or current pulses.

In order to avoid undesired capture of cardiac tissue, power pulses 140 and communication pulses 142 are sub-threshold pulses. In particular, power pulses 140 and communication pulses 142 have an amplitude and/or width inadequate to capture surrounding cardiac tissue. In exemplary embodiments, the amplitude of power pulses 140 is approximately +/−3 V, and the amplitude of communication pulses 142 is approximately 200 mV. In some embodiments, the amplitudes of pulses 140 and 142 are as little as approximately 150 mV.

Further, the widths of pulses 140, 142 are preferably less than 30 microseconds, and more preferably less than 10 microseconds. In embodiments in which power pulses 140 or communication pulses 142 are biphasic pulse pairs, the interval between pulses of a pair is also preferably less than 30 milliseconds, and more preferably less than 10 milliseconds. For ease of illustration, only a single power pulse 140 and communication pulses 142 is labeled in FIG. 11.

In exemplary embodiments, the energy storage element of sensor 32 is charged by power pulse 140 instead of pacing pulses 80. In such embodiments, sensor 32 decouples the energy storage element from conductors 40 during delivery of pacing pulses 80. IMD 14B provides a signal to sensor 32 via conductors 40 that indicates an upcoming delivery of a pacing pulse 80. In response, sensor 32 decouples the energy storage element from conductors 40 in response to the signal. For example, IMD 14B may alert sensor 32 to an upcoming pacing pulse 80 by varying the polarity of power pulse pairs 140 in a pattern that is recognized by sensor 32, such as the pattern of polarity variation of the three biphasic power pulse pairs 140 illustrated by FIG. 11. In some embodiments, IMD 14B provides a variety of signals or commands to sensor 32, such as commands to recouple the energy storage element to conductors 40, sample a physiological parameter value, or transmit data to IMD 14B, through variation of the polarity of power pulses 140.

In exemplary embodiments, IMD 14B and sensor 32 communicate by modulating the amplitude or, as shown in FIG. 11, the width of communication pulses 142 on conductors 40. In other embodiments, IMD 14B and sensor 32 communicate by modulating the length of intervals between communication pulses 142. In some embodiments, both IMD 14B and sensor 32 place communication pulses 142 on conductors 40. In some pulse width modulation embodiments, on the other hand, IMD 14B pulls up the voltage on conductors 40 and either IMD 14B or sensor 32 pulls down the voltage to signal a logic "1" or "0." In exemplary embodiments, power pulses 140 and communication pulses 142 are placed on the conductors 40 during refractory periods 86 to avoid undesired capture of cardiac tissue.

In some embodiments, the IMD 14 and sensor 32 communicate according to a communication protocol that provides a message format that includes one or more of start bits, address bits, pre-defined command bits, data bits, stop bits, and error-checking bits. In some embodiments, such a protocol includes unicast, multicast, and broadcast addressing of a plurality of sensors 32 carried by a single lead 12. In exemplary embodiments, sensor 32 synchronizes a clock it maintains to control the timing of communication and physiological parameter value sampling functions to a clock maintained by IMD 14B based on communication pulses 142 placed on conductors 40 by IMD 14B, e.g., the rising edge of communication pulses 142.

Multiple messages can be communicated between IMD 14B and sensor 32 during a single cardiac cycle or, preferably, refractory period 86. IMD 14B can deliver a train of one or more power pulses 140 at any time relative to such messages, e.g., before, after, and/or between. In some embodiments, IMD 14B determines a number of power pulses 140 to send based on an estimation of the power needed by sensor 32 to perform an action requested by one or more messages. Sensor 32 may provide an indication to IMD 14B as part of a message when more power is needed, and IMD 14B provides power pulses 140 in response to the low-power indication. Further details regarding an exemplary two-wire bus, pulse width modulation communication protocol involving delivery of power pulses, which may be employed by IMD 14B and sensor 32 according to some embodiments of the invention, may be found in commonly-assigned and co-pending U.S. patent application Ser. No. 10/733,000, filed Dec. 11, 2003, and entitled "IMPLANTABLE MEDICAL DEVICE COMMUNICATION SYSTEM WITH PULSED POWER BIASING."

Figure 12:
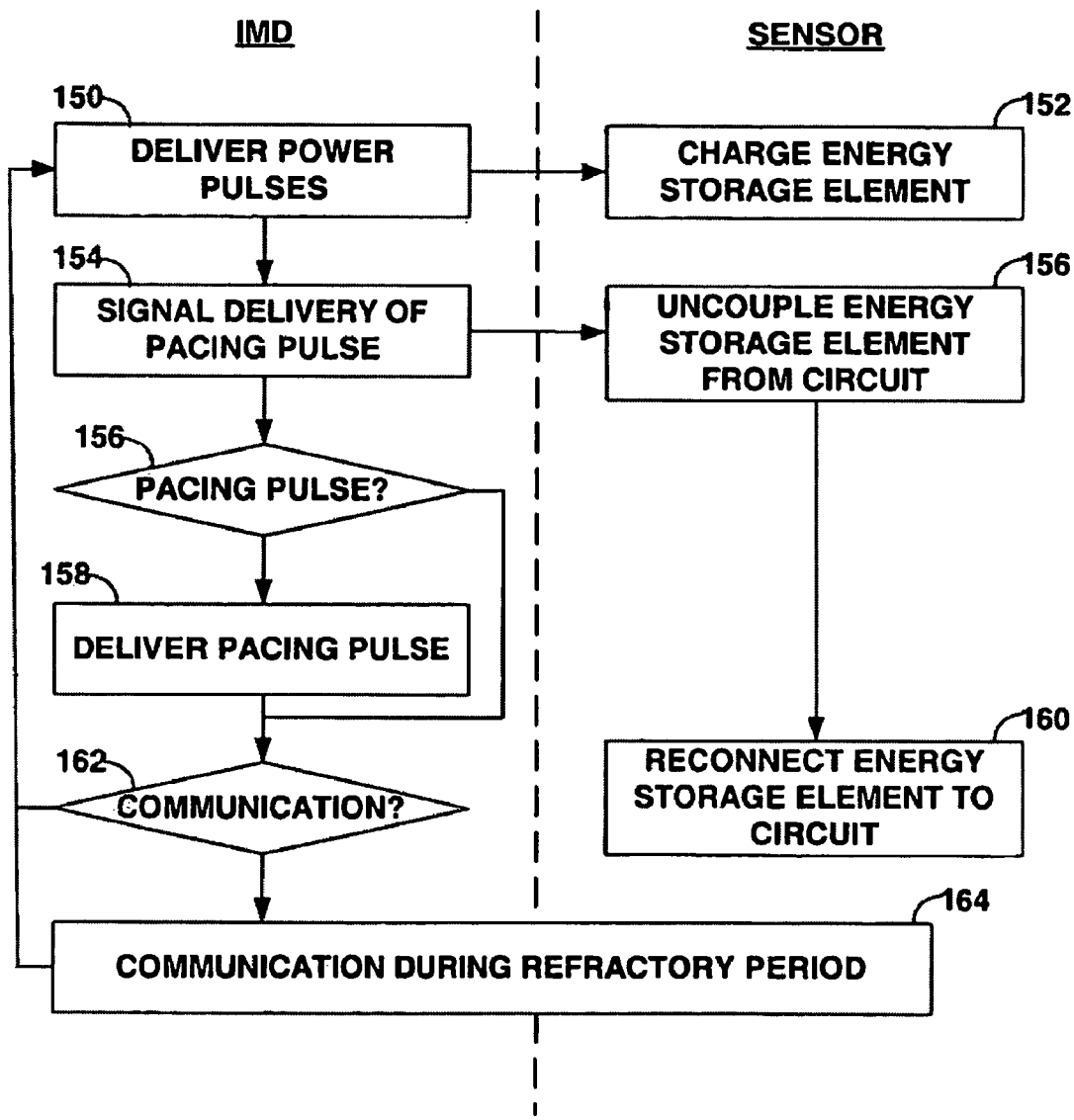
FIG. 12 is a flow diagram further illustrating delivery of power from an implantable medical device to a sensor and communication between the implantable medical device and the sensor according to the example embodiment of FIG. 11.

FIG. 12 is a flow diagram illustrating an example method for delivery of power from IMD 14B to sensor 32, and communication between IMD 14B and sensor 32 according to the example embodiment of FIG. 11. According to the method, IMD 14B delivers power pulses 140, which are preferably biphasic pulse pairs, to sensor 32 via conductors 40 (150). An energy storage element of sensor 32 that is coupled to conductors 40 is charged by the pulses (152). In some embodiments, sensor 32 includes a rectifier circuit that allows the energy storage circuit to be charged by biphasic power pulses 140.

At some time prior to scheduled delivery of a cardiac pacing pulse 80, e.g., near the end of an escape interval maintained by IMD 14B, IMD 14B signals an upcoming delivery of a pacing pulse 80 to sensor 32 (154). IMD 14B signals the upcoming pacing pulse by, for example, varying the polarity of power pulses 140, or sending a message to sensor 32 via communication pulses 142. In response to detecting the signal or receiving the message, sensor 32 uncouples the energy storage element from conductors 40 to avoid diverting stimulation energy from the patient (156).

If IMD 14B determines that a pacing pulse 80 is to be delivered (156), IMD 14B delivers a pacing pulse 80 (158). IMD 14B may determine that a pacing pulse 80 is to be delivered when an escape interval counter maintained by IMD 14B expires prior to detection of an intrinsic cardiac depolarization 82. Whether or not IMD 14B actually delivers a pacing pulse 80, sensor 32 recouples the energy storage element to conductors 40 (160). Sensor 32 recouples the energy storage element to conductors 40 at a fixed time after uncoupling the energy storage element from conductors 40, or in response to receiving a signal or message from IMD 14B directing sensor 32 to recouple the energy storage element. Further, if IMD 14B determines that communication with sensor 32 is to occur (162), IMD 14B initiates communication with sensor 32 during the refractory period 86 after the paced or intrinsic depolarization (164). IMD 14B determines that communication with sensor 32 is to occur when an updated value related for one or more physiological parameters is needed, Like IMD 14A discussed above, in some embodiments IMD 14B temporarily suspends one or more functions during delivery of power pulses 140 to sensor 32, and communication with sensor 32 via communication pulses 142. For example, as discussed above, IMD 14B may temporarily suspend one or more impedance or voltage measurement related functions, such as lead impedance measurement, battery life estimation, thoracic impedance measurement, minute ventilation measurement, P-wave sensing, R-wave sensing, or T-wave sensing.

Various embodiments of the invention have been described. These and other embodiments are within the scope of the following claims.

The invention claimed is:

1. An implantable medical device comprising:
   signal generation circuitry that delivers power to a sensor carried by an implantable medical lead that is connected to the implantable medical device, wherein the lead includes at least one conductor that is coupled to an electrode and the sensor, and the signal generation circuitry delivers power to the sensor via the conductor; and
   a processor to control delivery of power by the signal generation circuitry, communicate with the sensor via the conductor, and suspend a function of the implantable medical device during at least one of delivery of power to the sensor or communication with the sensor; and
   a therapy delivery module that delivers stimulation to a patient via the conductor and the electrode,
   wherein the processor provides a signal to the sensor via the conductor, the signal indicating an upcoming delivery of stimulation by the therapy delivery module, and wherein the sensor disconnects an energy storage element from the conductor in response to the signal.

2. The implantable medical device of claim 1, wherein the processor suspends at least one of autocapture detection, lead impedance measurement, battery life estimation, thoracic impedance measurement, minute ventilation measurement, P-wave sensing, R-wave sensing, or T-wave sensing.

3. The implantable medical device of claim 1, wherein the therapy delivery module measures at least one of voltage, current, or impedance during delivery of stimulation, and the processor receives data from the sensor by detecting coupling of a load to the conductor by the sensor during delivery of stimulation based on the measured voltage, current, or impedance.

4. The implantable medical device of claim 1, wherein the implantable medical device comprises a cardiac pacemaker, and the processor controls delivery of power by the signal generation circuitry and communicates with sensor during a refractory period of the patient.

5. An implantable medical device comprising:
   signal generation circuitry that delivers power to a sensor carried by an implantable medical lead that is connected to the implantable medical device, wherein the lead includes at least one conductor that is coupled to an electrode and the sensor, and the signal generation circuitry delivers power to the sensor via the conductor; and
   a processor to control delivery of power by the signal generation circuitry, communicate with the sensor via the conductor, and suspend a function of the implantable medical device during at least one of delivery of power to the sensor or communication with the sensor; and
   a therapy delivery module that delivers stimulation to a patient via the conductor and the electrode,
   wherein the therapy delivery module comprises the signal generation circuitry, and delivers power to the sensor as part of the delivered stimulation, and
   wherein the processor controls the therapy delivery module to increase an amplitude of the stimulation during delivery of power.

6. An implantable medical lead comprising:
   a first electrode;
   an electrical conductor electrically coupled to the first electrode; and
   a sensor coupled to the conductor in series with a current path between the first electrode and a second electrode not carried by the lead,
   wherein the sensor receives power from an implantable medical device and communicates with the implantable medical device via the conductor and the current path, and includes an energy storage element to store power received from the implantable medical device, and
   wherein the implantable medical device at least one of delivers electrical stimulation to a patient or senses electrical activity within the patient by the via the conductor and the electrode.

7. The implantable medical lead of claim 6, wherein the first electrode comprises a tip electrode for delivering cardiac pacing pulses from the implantable medical device cardiac tissue and sensing electrical activity of a heart of the patient.

8. The implantable medical lead of claim 6, wherein the energy storage element is selectively coupled in parallel with the implantable medical device to receive power from the implantable medical device, and the sensor includes a communication module that is selectively coupled in parallel with the implantable medical device for communication with the implantable medical device.

* * * * *